United States Patent [19]

Collins

[11] Patent Number: 5,251,621
[45] Date of Patent: Oct. 12, 1993

[54] ARRHYTHMIA CONTROL PACER USING SKELETAL MUSCLE CARDIAC GRAFT STIMULATION

[75] Inventor: Kenneth A. Collins, Neutral Bay, Australia

[73] Assignee: Telectronics Pacing Systems, Inc., Englewood, Colo.

[21] Appl. No.: 809,913

[22] Filed: Dec. 18, 1991

[51] Int. Cl.$^5$ .................................. A61N 1/368
[52] U.S. Cl. ............................. 607/4; 600/17; 607/6
[58] Field of Search ............... 128/419 PG; 600/16, 600/17; 623/3

[56] References Cited

U.S. PATENT DOCUMENTS

| | | | |
|---|---|---|---|
| 3,371,662 | 3/1968 | Heid et al. | 128/24.5 |
| 3,942,534 | 3/1976 | Allen et al. | 128/419 PG |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,411,268 | 10/1983 | Cox | 128/421 |
| 4,735,205 | 4/1988 | Chachques et al. | 128/419 PG |
| 4,791,911 | 12/1988 | Magovern | 600/36 |
| 4,869,252 | 9/1989 | Gilli | 128/419 PG |
| 4,925,443 | 5/1990 | Heilman et al. | 128/419 D |
| 5,009,229 | 4/1991 | Grandjean et al. | 128/419 P |
| 5,069,680 | 12/1991 | Grandjean | 600/16 |
| 5,161,527 | 11/1992 | Nappholz et al. | 128/419 PG |

Primary Examiner—William E. Kamm
Assistant Examiner—Kennedy J. Schaetzle
Attorney, Agent, or Firm—Gottlieb, Rackman & Reisman

[57] ABSTRACT

An antiarrhythmia pacemaker and method detect and confirm the occurrence of an abnormal condition of a patient's heart selected from the group comprising tachycardia, fibrillation and precursors thereof, and, in response thereto, deliver an antiarrhythmia therapy to the patient which includes two components, electrical stimulation of the heart and electrical stimulation of a skeletal muscle graft which has been surgically grafted to the heart to augment performance of the heart. The antiarrhythmia pacemaker and method control electrical stimulation of the heart in terms of timing, frequency, amplitude, duration and other operational parameters, to provide such pacing therapies as antitachycardia pacing, cardioversion and defibrillation. A skeletal muscle graft stimulation electrode, which is driven by a skeletal muscle pulse stimulator, stimulates preselected nerve fibers within the skeletal muscle graft. An arrhythmia therapy control responds to the detection and confirmation of an abnormal heart condition by controlling and coordinating the operation of the heart stimulator and the skeletal muscle graft stimulator to direct performance of a combined heart stimulation and skeletal muscle graft stimulation therapy.

19 Claims, 12 Drawing Sheets

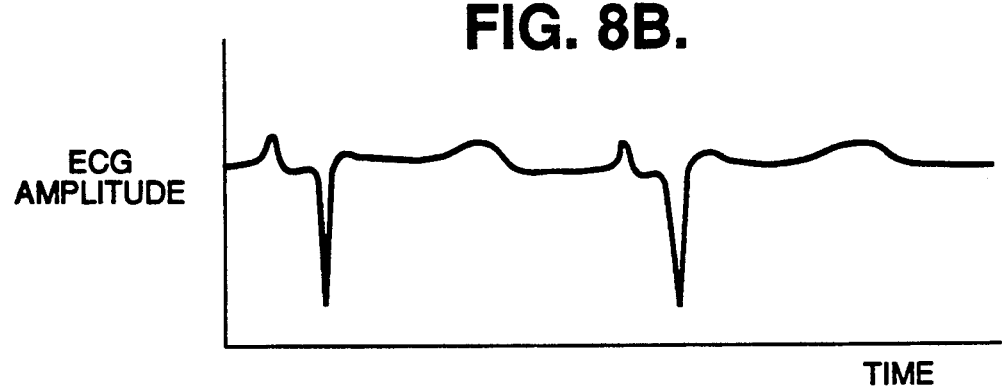
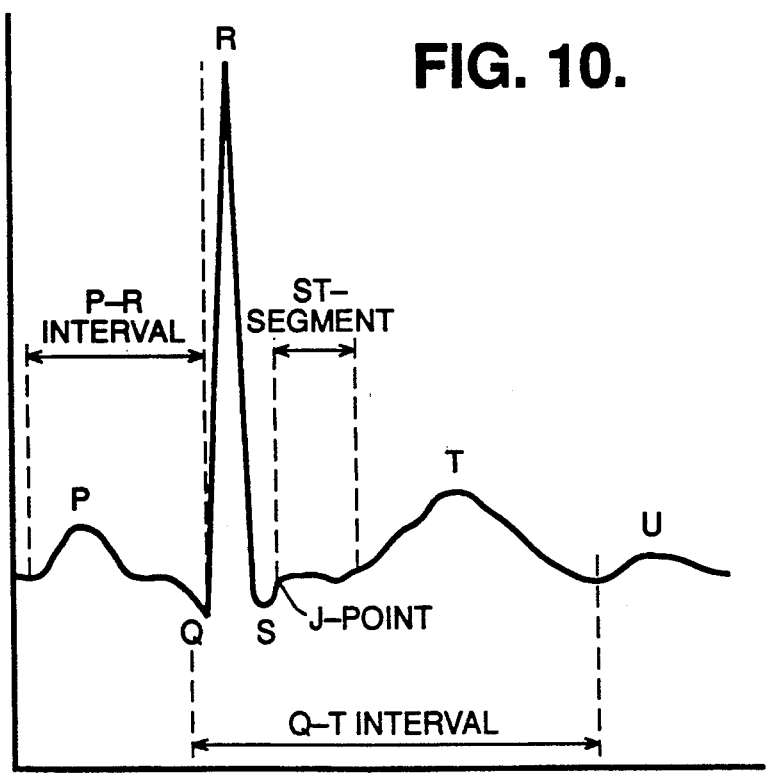

ARRHYTHMIA CONTROL PACER USING SKELETAL MUSCLE CARDIAC GRAFT STIMULATION

TECHNICAL FIELD

This invention relates to a combined muscle stimulator and antiarrhythmia pacing apparatus and its method of operation for detecting abnormalities of a patient's heart and, in response to such detection, administering an antiarrhythmia therapy. More particularly, this invention relates to an antiarrhythmia pacing apparatus and method that employs an antiarrhythmia therapy which comprises the coordination, control and generation of stimulation pulses to both the patient's heart and to a muscle graft that has been previously attached to the heart.

BACKGROUND OF THE INVENTION

Severe chronic cardiac insufficiency arising from cardiac disease or injury shortens and degrades the quality of life of many patients. One form of severe chronic cardiac insufficiency, congestive heart failure, is a pathophysiological state in which cardiac output is inadequate to meet physiological requirements of the body. The mortality rate for congestive heart failure is greater than 50% within 5 years of onset. Treatments for severe chronic cardiac insufficiency include heart transplants, artificial heart implants and cardiomyoplasty. Cardiac transplantation, using cyclosporine to inhibit tissue rejection, is a very successful technique for prolonging a cardiac patient's life, improving the survival rate to 80% at 1 year. However, the transplant operation is very expensive and heart availability is limited. The artificial heart has had very limited success.

Dynamic cardiomyoplasty is a surgical and electrical therapeutic technique in which a skeletal muscle flap is dissected from a patient, while maintaining its innervating neural tissues and neurovascular structures, and surgically placed around the patient's heart. An electrical stimulation device with an electrical pulse generator and intramuscular electrodes is implanted which performs muscle electrical stimulation in synchrony with ventricular systole to support cardiac pumping.

Stimulated skeletal muscle transforms into a fatigue-resistant state suitable for chronic ventricular assistance, enabling dynamic cardiomyoplasty. This permits substitution of skeletal muscle for a patient's ailing heart muscle. The skeletal muscle is then trained to function in the manner of cardiac muscle to increase the patient's cardiac output. Sequential and progressive skeletal muscle electrical stimulation causes glycolytic muscle fibers, predominant in skeletal muscle, to take the form of oxidative fibers. Oxidative fibers are resistant to fatigue and have histochemical and biochemical characteristics of myocardium.

G. J. Magovern, in U.S. Pat. No. 4,791,911, entitled "Method of Cardiac Reconstructive Surgery", issued Dec. 20, 1988, discloses a surgical method of reconstructing damaged cardiac muscle using a latissimus dorsi skeletal muscle autograft.

U.S. Pat. No. 4,411,268 to J. A. Cox, entitled "Muscle Stimulator," which issued Oct. 25, 1983, describes a pulse generator which delivers conditioning and stimulating pulses to a cardiac muscle graft. These pulses are delivered in synchrony with either the delivery of stimulating pulses to the heart or the sensing of natural heartbeats.

Further detail on the muscle stimulator technique and intracardiac leads for practicing cardiomyoplasty are described in U.S. Pat. No. 4,735,205, by J. C. Chachques et al., entitled "Method and Apparatus Including a Sliding Insulation Lead for Cardiac Assistance", issued Apr. 5, 1988.

Cardiac arrhythmias create one problem that arises with the muscle stimulation techniques. Patients with severe chronic cardiac insufficiency are susceptible to serious arrhythmias. One such arrhythmia is a tachycardia. Cardiac tissue is susceptible to tachycardia episodes if two conditions occur. First, more than one electrical impulse pathway through the heart exists to allow for the presence of circus movement. Second, conduction times and refractory periods within the multiple pathways must be different. One characteristic of reentrant tachycardias is that the cardiac tissue ahead of the impulse is not refractory, allowing the tachycardia to perpetuate itself, and the cardiac tissue behind the impulse is variable or inconsistent with respect to refractory nature. The tissue damage inherent in cases of severe chronic cardiac insufficiency and congestive heart failure promotes the conditions associated with a tachycardia-susceptible cardiac state.

Antitachycardia pacers, cardioverters and defibrillators have been developed to detect arrhythmia episodes and generate an electrical stimulation therapy to terminate such episodes.

Antitachycardia pacers terminate reentrant tachycardias by delivering an electrical stimulation pulse to the heart while cardiac tissue is in a refractory state. The pulse is exactly timed to interrupt a reentrant circuit so that the anterograde limb of the circuit is refractory (so that the tachycardia is not merely reset) and, at the same time, the retrograde limb is rendered refractory. Correct stimulation timing creates electrical charge propagation which penetrates both circuit limbs, interrupting the tachycardia in the one limb and failing to perpetuate the impulse through the other (anterograde) limb, which the impulse cannot enter because the portion of the circuit is refractory. Each of the three forms of antitachycardia pacing—underdrive, overdrive and refractory pacing (also called "extrastimulus pacing")—are attempts to find this correct stimulation timing.

Underdrive pacing is pacing at a rate which is slower than the rate of a tachycardia. Overdrive pacing occurs at a rate which is faster than the tachycardia rate. One problem with underdrive and overdrive pacing is that pulses are delivered asynchronously with respect to the natural impulse propagation of the tachycardia. A long period of therapy may be required before the appropriate stimulus is delivered. Furthermore, these asynchronous methods do not allow the delivery of several successive appropriately timed stimuli. Most importantly, there exists a risk of generating a stimulus pulse during a time when the heart is vulnerable to aggravation of the tachycardia, possibly leading to fibrillation and sudden death.

Dual-demand antitachycardia pacing reduces some of the risk of aggravating an existing tachycardia by providing for automatic tachycardia recognition prior to initiating asynchronous competitive pacing. Only if the antitachycardia therapy is successful and the tachycardia is broken does the dual-demand pacer revert to normal demand pacing.

Further improvement is provided in a dual-chamber antitachycardia device which performs asynchronous competitive pacing (DOO pacing) which doubles the probability of offering an appropriately timed stimulus into the reentrant circuit.

Other, more recent, antitachycardia pacers provide for faster reversion of tachycardias by pacing using a technique of systematic scanning of diastole with single or double impulses, rather than pacing in an asynchronous manner.

Most recently, it was recognized that single impulses sometimes fail to terminate the tachycardia because the areas of refractoriness are interposed between the impulse and the reentrant circuit. An improved antitachycardia pacer employs multiple bursts of rapid impulses to reduce refractoriness and allow entry into the tachycardia circuit. One problem with burst pacing is the increased possibility of pacing during a vulnerable period, leading to tachycardia acceleration and fibrillation. Burst pacers may not be appropriate for automatic, implanted pacing.

In general, antiarrhythmia pacing techniques are not always successful and there is the ever present risk of inducing or aggravating unwanted and possibly dangerous arrhythmias. Present day antitachycardia pacers cannot avoid the delay before initiating therapy which is required for tachycardia detection, recognition and application of treatment. This delay may allow autonomic nervous system sensors within the body to become stimulated, allowing sympathetic nerve activation which raises the heart rate and further alters the refractory nature of cardiac tissue, thereby rendering tachycardia termination more difficult.

Furthermore, it is impossible for antitachycardia pacers to immediately sense that a pacing therapy was successful, causing a delay in terminating the applied therapy. Delivery of unnecessary therapy pulses after a previous extrastimulus pulse has terminated a tachycardia may cause its reinitiation.

A better understanding of the physiological processes underlying the genesis and aggravation of cardiac arrhythmias may lead to an improved treatment for arrhythmia prevention and termination. One such physiological process involves severely reduced blood flow to the heart muscle, called myocardial ischemia. Evidence shows that ischemia causes arrhythmias, including tachycardias and fibrillation, and may lead to sudden cardiac death. Ischemia generates ventricular arrhythmias by way of three main mechanisms. First, ischemia cause automaticity of the myocardial tissue. Automaticity is the propensity to initiate and generate spontaneous ectopic action potentials. Second, the heart develops reentrant circuits via electrical heterogeneity. Here, conduction of action potentials slows in particular ischemia-damaged areas of the heart, resulting in the development of reentry and re-excitation of electrical impulses within the cardiac tissues. Finally, abnormalities of repolarization, such as early and late after-depolarizations further aggravate ventricular arrhythmias. This occurs because, throughout the heart, a variable lengthening or shortening of the refractory periods causes an increased dispersion of refractoriness between ischemic and nonischemic zones.

In this manner, ischemia causes a ventricular tachycardia, in which insufficient time between heartbeats is allowed for diastolic filling. Thus, cardiac output will fall, further aggravating ischemia and leading to the risk of acute myocardial ischemia. Ischemia predisposes the heart to development of totally disorganized ventricular rhythm, called ventricular fibrillation, in which regular cardiac pumping ceases and sudden cardiac death will develop.

The present invention proposes a therapy for preventing and terminating cardiac arrhythmias which may lead to ventricular fibrillation and sudden death in patients suffering from congestive heart failure. The proposed therapy combines antiarrhythmia pacing of various forms with skeletal muscle graft stimulation. Muscle graft stimulation increases cardiac output, aortic pressure and, therefore, perfusion of the heart to alleviate myocardial ischemia and ameliorate arrhythmias.

One group of prior art cardiac assist devices, antiarrhythmia pacing systems, employs electrical stimulus generation to treat cardiac arrhythmias. (See, e.g., U.S. Pat. No. 4,390,021 to R. A. J. Spurrell et al., which issued Jun. 28, 1983, and is entitled "Two Pulse Tachycardia Control Pacer"). Another group of prior art devices, skeletal muscle stimulators (also called "cardiomyostimulators"), utilizes muscle fiber stimulation to elevate cardiac output. (See e.g., U.S. Pat. No. 4,735,205 to J. C. Chachques et al., discussed earlier). While each of the foregoing devices provides satisfactory assistance in its intended therapy area, the therapy provided is insufficient with respect to the therapy area that the other device treats.

It is therefore a primary object of the present invention to provide a method and apparatus for detecting and treating various cardiac arrhythmias, in which treatment a combined antiarrhythmia therapy and skeletal muscle stimulation therapy is provided to terminate the arrhythmia.

Another object of the present invention is to improve the success rate of arrhythmia termination while decreasing the risks of aggravating arrhythmias which may occur when only heart pacing therapies are utilized.

An additional object of the present invention is to increase cardiac perfusion during arrhythmia episodes to ameliorate ischemia and avoid aggravation of the arrhythmia into a more dangerous form.

Further objects and advantages of the present invention will become apparent as the following description proceeds.

BRIEF SUMMARY OF THE INVENTION

In accordance with the principles of the present invention, an antiarrhythmia pacemaker is provided for stimulating a patient's heart that has a skeletal muscle grafted thereon to assist cardiac functions of the heart. The antiarrhythmia pacemaker includes a means for analyzing signals from the heart and detecting and classifying episodes of abnormal conditions of the heart. The pacemaker also includes a heart stimulating means for generating and delivering stimulating pulses of various amplitudes to the heart. These pulses may be characteristic of standard pacemaker stimulation, cardioversion or defibrillation shocks. The antiarrhythmia pacemaker also includes at least one muscle stimulation electrode which is adapted to be placed in electrical contact with the muscle graft. This electrode is empowered by a muscle pulse stimulating means which is electrically coupled to the muscle stimulation electrode. The muscle pulse stimulating means generates stimulating pulse trains which are delivered to the muscle and are sufficient in amplitude, duration and frequency to effect a desired contraction of the muscle.

In response to the detection and classification of an abnormal condition of the heart, the antiarrhythmia pacemaker activates a heart pacing and muscle stimulation control means which controls and synchronizes operations of the heart stimulating means and the muscle pulse stimulating means to direct a combined antiarrhythmia heart therapy and muscle stimulation therapy corresponding to the classification of abnormal condition determined by the detecting and classifying means. When the heart is not functioning in an abnormal condition, the antiarrhythmia pacemaker may contract the muscle in synchrony with the contraction of the heart to augment and strengthen the heart.

The antiarrhythmia pacemaker may combine and synchronize antitachycardia pacing therapy and muscle stimulation upon detecting a ventricular tachycardia condition. The pulse trains delivered to the skeletal muscle may be controlled to slow the cardiac rate from the tachycardia rate. Further, the pulse trains delivered to the skeletal muscle may be controlled to strengthen the muscle contraction for the purpose of increasing cardiac output of the heart and increasing lateral aortic blood pressure.

The antiarrhythmia pacemaker may combine and synchronize defibrillation therapy and muscle stimulation upon detecting a fibrillation condition. In cardiac cycles prior to and subsequent to the cardiac cycles within which defibrillation shocks are delivered, the pacemaker may control the muscle pulse stimulating means to generate and deliver stimulating pulse trains in which the pulse trains are synchronous to the timing of heart contractions but are generated for only a predetermined ratio of cardiac cycles. In this manner, the interval between muscle stimulation trains is greater than a predetermined tachycardia cycle interval limit. The duration of these pulse trains is greater than that of trains in which a fibrillation condition is not detected. Thus, fibrillation therapy pulse trains are provided which are sufficient to effect a less frequent but stronger contraction of the muscle.

The antiarrhythmia pacemaker responds to the detection of an arrhythmia to better ensure a prompt but safe arrhythmia termination without inducing prolonged periods of intricate electrical interactions between the arrhythmia and the pacemaker which sometimes occur in antiarrhythmia pacemakers relying on heart pacing alone. The body responds to tachycardias by complex autonomic reflex changes, including the release of catecholamines, which tend to oppose arrhythmia termination. The pacemaker of the present invention provides skeletal muscle stimulation to improve hemodynamics of the cardiovascular system and counteract these autonomic reflex changes.

The hemodynamic benefits of muscle stimulation improve myocardial contraction efficiency by augmenting cardiac output, without requiring the participation of myocardial fibers as is necessary with the use of cardiac assist devices which rely on electrical stimulation alone. Muscle stimulation provides a technique for improving cardiovascular hemodynamics, demanding a lesser burden on myocardial fibers and avoiding pacing stimulation of the heart at rates that aggravate existing arrhythmias. Thus, muscle stimulation and antiarrhythmia pacing are combined to aid prevention of ventricular tachyarrhythmias occurring in the presence of myocardial ischemia.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIGS. 8A and 8B are illustrations of samples of the detailed morphology of ECGs which are recognized as precursors to malignant cardiac arrhythmias, including premature ventricular depolarizations (FIG. 8A) and repolarization abnormalities such as long QT interval (FIG. 8B), detected by an antiarrhythmia pacemaker of the present invention;

FIG. 10 is an illustration of a normal electrocardiogram signal;

FIGS. 12A and 12B illustrate one method of combining antiarrhythmia pacing with skeletal muscle stimulation, in which FIG. 12A depicts waveforms for an electrocardiogram (ECG), an antitachycardia pacing stimulation (ATP) and a skeletal muscle stimulation (MS) when the heart is functioning with a normal sinus rhythm, and in which FIG. 12B depicts waveforms for an electrocardiogram (ECG), an antitachycardia pacing stimulation (ATP) and a skeletal muscle stimulation (MS) when the heart is functioning under ventricular tachycardia conditions.

DETAILED DESCRIPTION OF THE INVENTION

Figure 1:
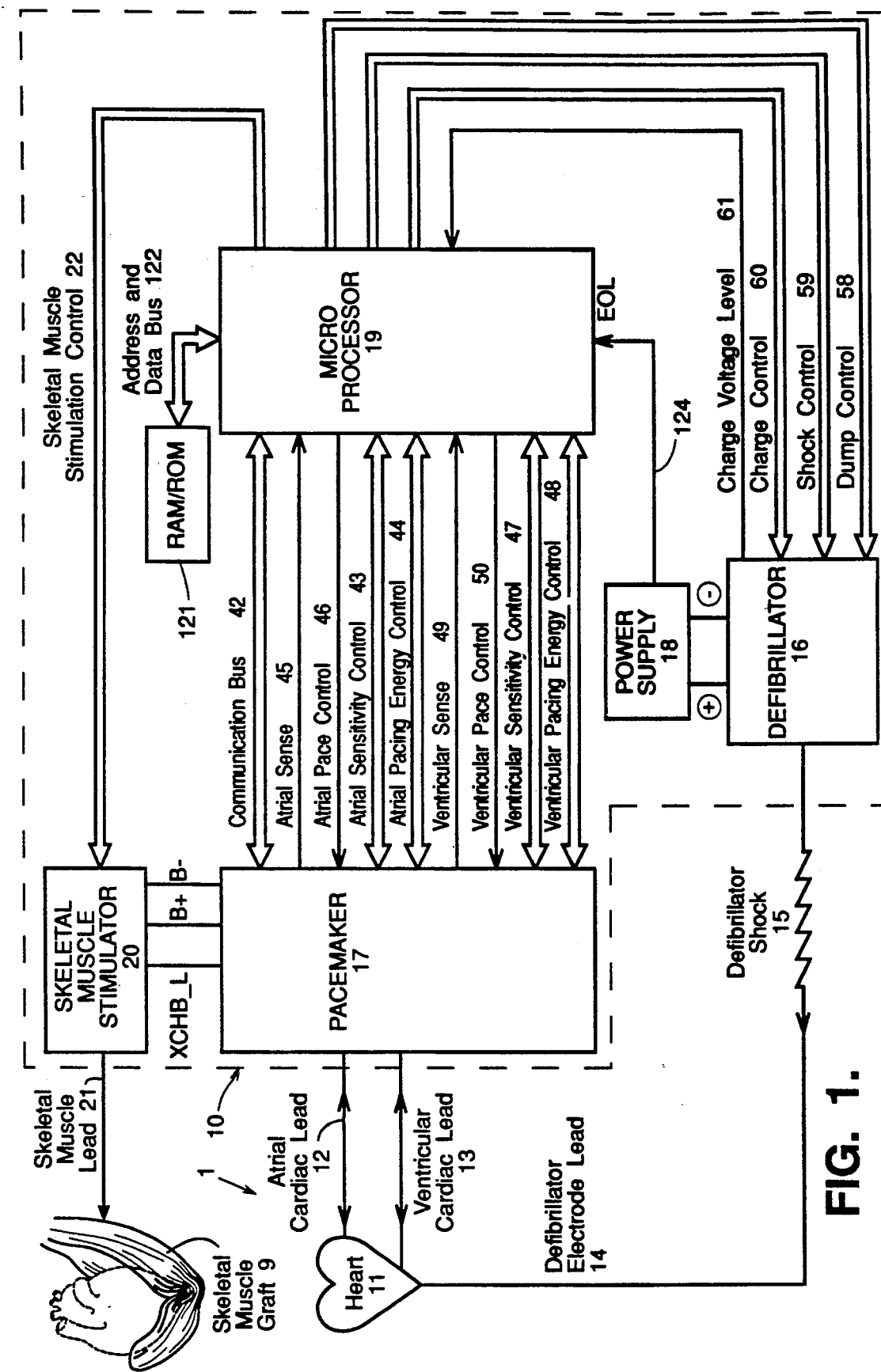
FIG. 1 is a block diagram of an implanted, rate-responsive, dual chamber arrhythmia control system (ACS) in accordance with the present invention.

Referring to FIG. 1, there is depicted a block diagram of an arrhythmia control system 1. System 1 is designed to be implanted within a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium, and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to pacemaker 17, skeletal muscle stimulator 20 and defibrillator 16; and a power supply 18 for the provision of a reliable voltage level to pacemaker 17, microprocessor 19, skeletal muscle stimulator 20 and defibrillator 16 by suitable electrical conductors (not shown). Skeletal muscle stimulator 20 generates electrical pulses on a skeletal muscle lead 21 for stimulating a skeletal muscle graft 9, such as a patient's latissimus dorsi muscle, according to timed control signals from microprocessor 19 communicated via skeletal muscle stimulation control bus 22. Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

Microprocessor 19 is connected to a random access memory/read only memory (RAM/ROM) unit 121 by an address and data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pacing energy control bus 44, a ventricular sense line 49, a ventricular pace control line 50, a ventricular sensitivity control bus 47, and a ventricular pacing energy control bus 48. Microprocessor 19 transmits control signals, according to the description below, over skeletal muscle stimulation control bus 22 to the skeletal muscle stimulator 20. As also more fully described below, microprocessor 19 is connected to defibrillator 16 by a charge voltage level line 61, a charge control bus 60, a shock control bus 59, and a dump control bus 58.

Figure 2:
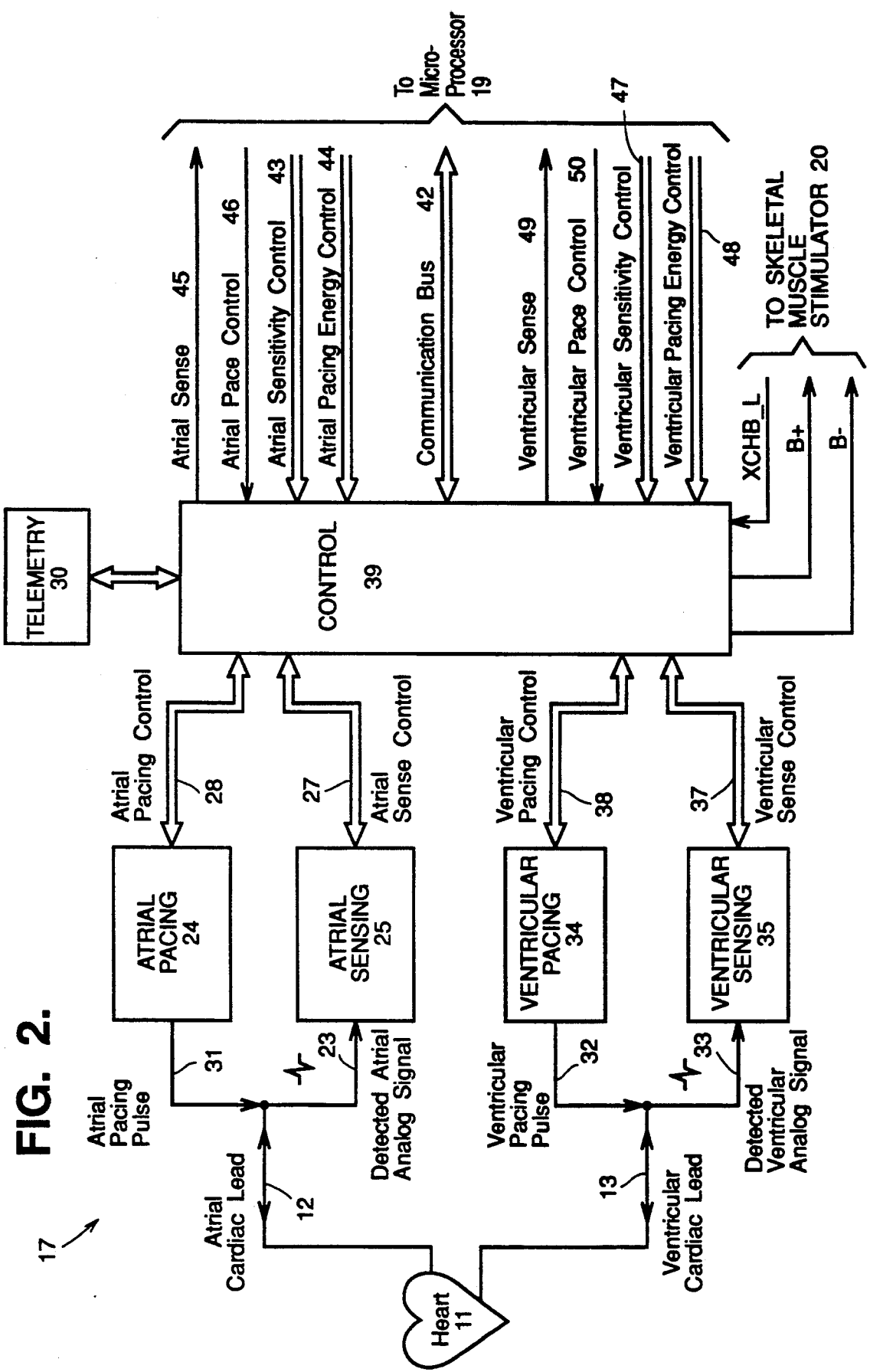
FIG. 2 is a block diagram of a pacemaker utilized in the system of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to be delivered to the heart via atrial pacing pulse lead 31 and atrial cardiac lead 12, and via ventricular pacing pulse lead 32 and ventricular cardiac lead 13, respectively. The atrial and ventricular pacing energy control inputs determine the respective magnitudes of the pacing pulse energy so delivered. The operation of the logic which changes the pulse energy is described in greater detail in U.S. Pat. No. 4,869,252 to Norma Louise Gilli, issued Sep. 26, 1989, and entitled "Apparatus And Method For Controlling Pulse Energy In Antitachyarrhythmia And Bradycardia Pacing Devices," which description is incorporated herein by reference.

Telemetry circuit 30 provides a bidirectional link between control block 39 of pacemaker 17 and an external device such as a programmer. It allows data such as the operating parameters to be read from or altered in the implanted module 10.

Figure 3:
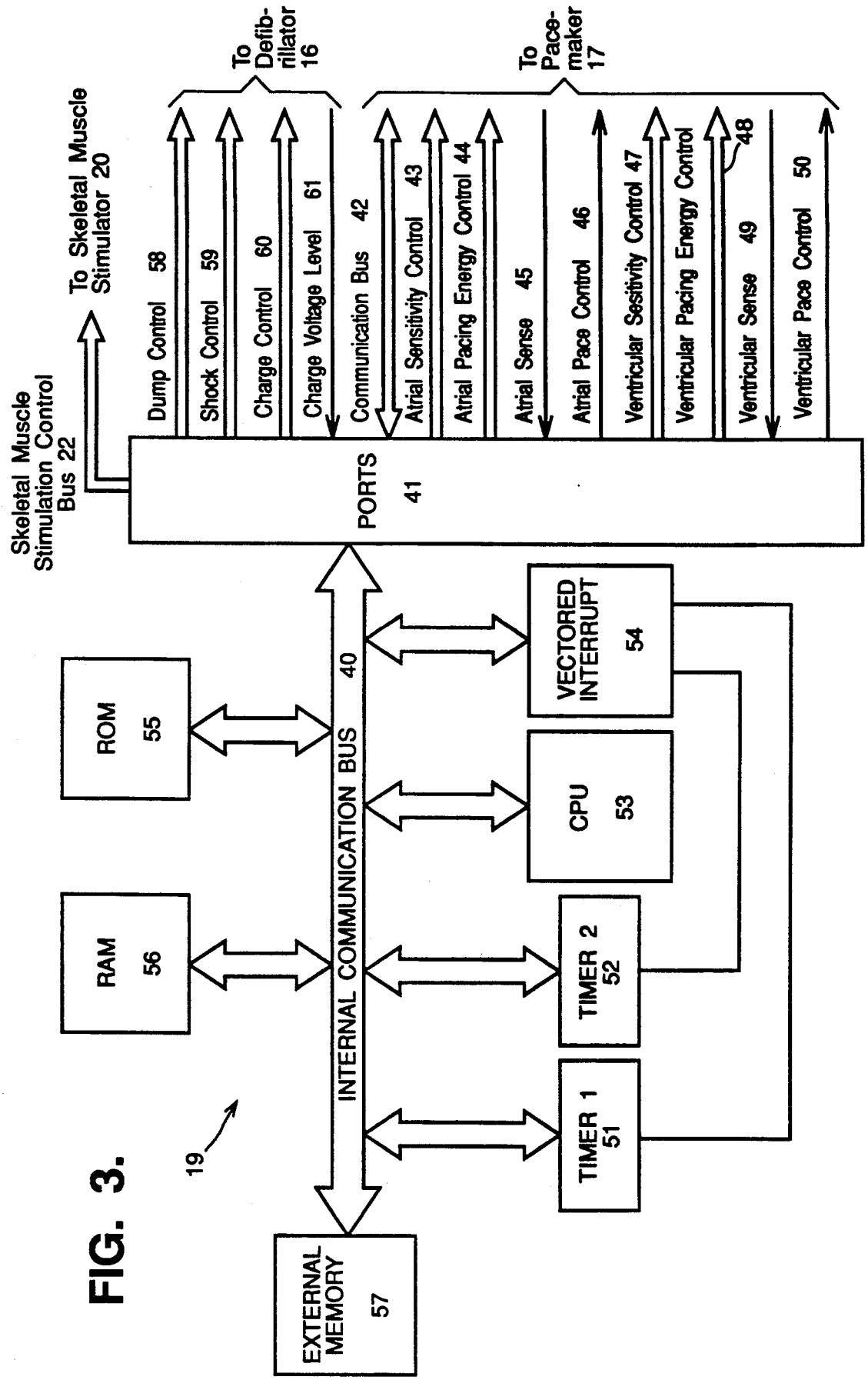
FIG. 3 is a block diagram of a microprocessor utilized in the system of FIG. 1.

Referring to FIG. 3, microprocessor 19 comprises two 16-bit timers 51 and 52, a CPU 53, a vectored interrupts block 54, a ROM 55, a RAM 56, an external memory 57, a ports block 41 and an internal communications bus 40. RAM 56 acts as a scratch pad and active memory during execution of the various programs stored in ROM 55 and used by microprocessor 19. These programs includes system supervisory programs, detection algorithms for detecting and confirming various arrhythmias, and programming for implementing the logic flow diagrams of FIG. 6 and FIG. 11, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communication bus 42 serves to provide signals indicative of such control to microprocessor 19. Thus, it is also possible for an external programmer to control operation of the skeletal muscle stimulator 20 and the defibrillator 16 by means of signals provided to microprocessor 19.

Appropriate telemetry commands may cause telemetry circuit 30 to transmit data to the external programmer. Data stored is read out, by microprocessor 19, on to communication bus 42, through control block 39 in pacemaker 17, and into telemetry circuit 30 for transmission to the external programmer by a transmitter in telemetry circuit 30.

Microprocessor 19 receives various status and/or control inputs from the pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, the shock control on bus 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. In addition, the microprocessor 19 controls all aspects of skeletal muscle stimulation, as will be described in detail below, by formulating control signals and transmitting these signals over the skeletal muscle stimulation control bus 22 to skeletal muscle stimulator 20. Charge voltage level line 61 provides a digital signal representative of charge voltage from an analog-to-digital converter within defibrillator 16, thus providing a feedback loop which assures that a shock of proper energy level is delivered by defibrillator 16.

Figure 4:
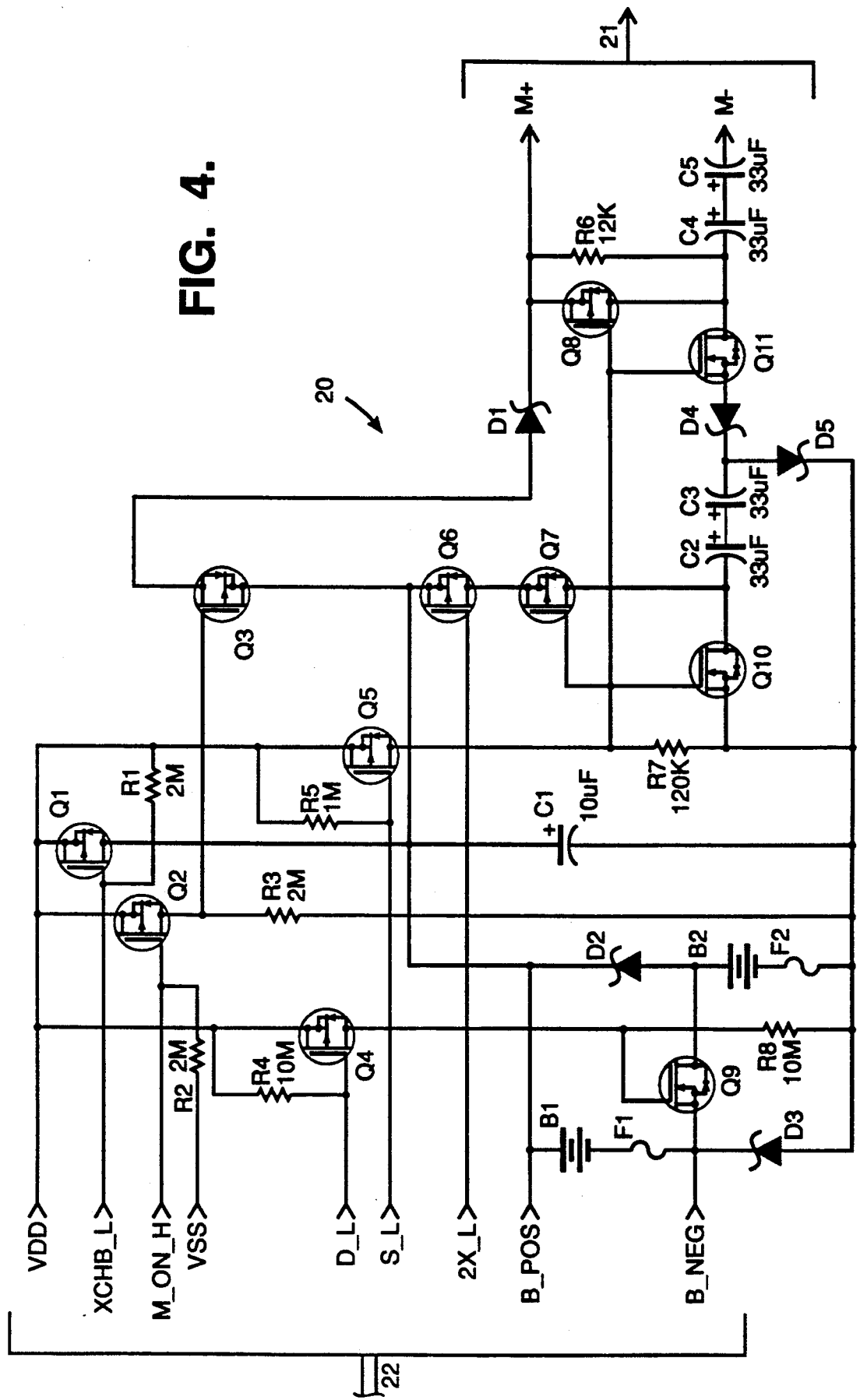
FIG. 4 depicts a circuit schematic of a skeletal muscle stimulator utilized in the system of FIG. 1.

Referring to FIG. 4, the skeletal muscle stimulator 20 receives input signals from microprocessor 19 over the skeletal muscle stimulation control bus 22. These signals include power (VDD), which is typically an amplitude of 2.8 V, and ground reference (VSS) as well as control signals S_L, 2X_L, D_L, XCHB_L and M_ON_H. The pacemaker 17 supplies battery power B_POS and B_NEG which provides energy for biphasic skeletal muscle stimulation. In the preferred embodiment of the present invention, the B_POS amplitude is about 3 V. The battery voltages B_POS and B_NEG are floating with respect to circuit power VDD to prevent variations in circuit energy during different parts of the cardiac cycle caused by inconsistent demands on the battery from the pacing pulse and skeletal muscle stimulation pulse generation circuits.

XCHB_L, a cross channel blanking control signal from the microprocessor 19, is also supplied to a sense blanking input of the pacemaker 17 to disable pacemaker sensing during generation of a skeletal muscle stimulation pulse. This prevents the pacemaker 17 from incorrectly classifying a skeletal muscle stimulation pulse as an episode of intrinsic cardiac activity.

The circuit of FIG. 4, in response to codes written from the microprocessor 19, produces biphasic skeletal muscle stimulation pulses on the skeletal muscle lead, M+ and M−. All characteristics of the skeletal muscle stimulation pulses: the timing, frequency, burst duration, amplitude, pulse width, and pulse morphology, are determined by the microprocessor. FIG. 4 circuitry merely responds to these input codes by producing a particular amplitude and polarity signal on the M+ and M− leads. In this manner, the microprocessor generates the characteristics of the skeletal muscle stimulation pulses according to the timing of codes written to the skeletal muscle stimulation control bus 22.

Figure 5:
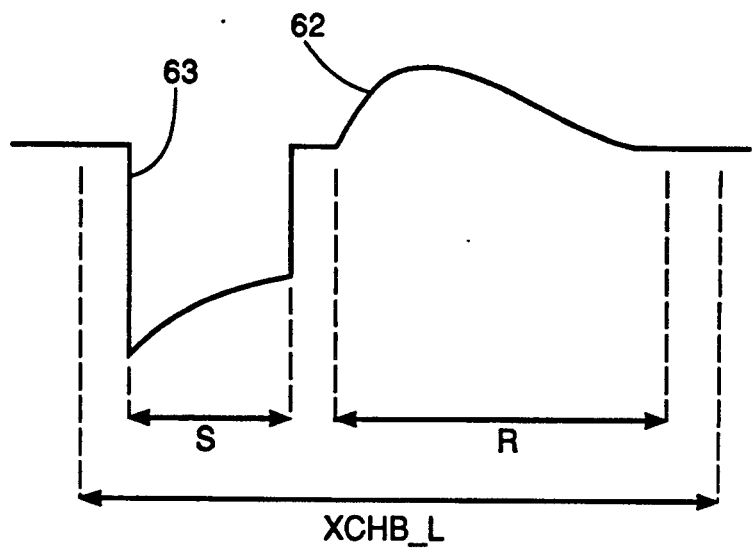
FIG. 5 depicts the form of a biphasic skeletal muscle stimulation pulse generated by the circuit of FIG. 4.

Input signal lines S_L, M_ON_H and XCHB_L contain skeletal muscle pulse enable and polarity control signals which are dynamic in the sense that the microprocessor 19 writes and times the codes written to these lines to produce a particular amplitude for a predetermined duration. The microprocessor enables the circuit of FIG. 4 to produce an output on one or the other of leads M+ and M− by setting input signal line M_ON_H to 1 which, by means of control by p-channel switching field effect transistor Q3, applies either B_POS or B_NEG battery power to the corresponding leads M+ and M−, depending on the signal on input input signal line S_L. The microprocessor controls the stimulus pulse timing and width by setting a signal on input signal line S_L for a predetermined time and duration. When the microprocessor writes a 0 value to input signal line S_L while a 1 value is on input signal line M_ON_H, the outputs of p-channel switching field effect transistors Q7 and Q8 are enabled to enable the M+ lead, and the outputs of n-channel switching field effect transistors Q10 and Q11 are disabled to disable the M− lead, producing a positive polarity output pulse, having a duration R, as shown at 62 in FIG. 5. Alternatively, the microprocessor may write a 1 value to line S_L to disable field effect transistors Q7 and Q8 and enable transistors Q10 and Q11 to produce a negative polarity output pulse, having a duration S, as shown at 63 in FIG. 5. If the value applied to input signal line M_ON_H is 0, neither lead M+ nor lead M− are energized and the skeletal muscle stimulator does not produce a pulse. If the value on input signal line M_ON_H is set to 1 and S_L is set to 0, line M+ is energized and the skeletal muscle stimulator produces a positive polarity pulse 62, as shown in FIG. 5. The duration R is a programmable parameter for the microprocessor. If the initial value on line M_ON_H is set to 1 and the value on line S_L is set to 1, lead M− is energized and the skeletal muscle stimulator produces a negative polarity pulse 63, having the duration S of FIG. 5. Stimulus duration S is a programmable parameter for the microprocessor. The microprocessor controls line XCHB_L to set the timing and duration of the sense blanking input of the pacemaker 17 to disable pacemaker sensing during generation of a skeletal muscle stimulation pulse. Cross channel blanking duration may be a programmable parameter for the microprocessor.

Input signal lines D_L and 2X_L contain skeletal muscle pulse amplitude control signals which are static in the sense that the microprocessor writes them, at most, only once per cycle. Normally, the microprocessor only writes amplitude control signals upon reprogramming, via telemetry, by an external communicating device. Line D_L is utilized as a battery voltage doubler. Line 2X_L is utilized as a stimulus voltage doubler. Thus, lines D_L and 2X_L remain at the same settings throughout numerous cardiac cycles, while the skeletal muscle pulse that is generated has a negative, positive or zero polarity. When the microprocessor sets line D_L to 1 ("on"), the n-channel switching field effect transistor Q9 enables doubling of the battery voltage. In a similar manner (but with an opposite polarity), when the microprocessor sets line 2X_L to 0 ("on"), the p-channel switching field effect transistor Q9 enables doubling of the stimulus voltage. Therefore, when the microprocessor sets line D_L "off" (O) and line 2X_L "off" (1), the amplitude of the skeletal muscle stimulation pulse is equal to the battery voltage, 3 V in the preferred embodiment of the invention. When the microprocessor sets line D_L "on" (1) and line 2X_L "off" (1), the amplitude of the skeletal muscle stimulation pulse is equal to twice the battery voltage (6 V). When the microprocessor sets line D_L "on" (1) and line 2X_L "on" (O), the amplitude of the skeletal muscle stimulation pulse is equal to four times the battery voltage (12 V).

Referring again to FIG. 1, when the microprocessor 19 determines that skeletal muscle graft stimulation is appropriate, it works in conjunction with the skeletal muscle stimulator 20 to produce pulses or bursts of pulses, which are applied to the skeletal muscle graft 9. The microprocessor may time these pulses or bursts of pulses with respect to intrinsic or paced cardiac activity which is sensed or generated, respectively, by the pacemaker 17. This mode of skeletal muscle stimulation is termed "synchronous" skeletal muscle stimulation. Alternatively, the microprocessor 19 may time the pulses or bursts of pulses according to the operations of an internal timer, wherein the stimulation occurs asynchronously with respect to individual cardiac events.

According to "synchronous" programming of the microprocessor 19, when the pacemaker 17 detects either a natural atrial or a natural ventricular intrinsic event it will send a signal to the microprocessor 19 via atrial sense line 45 or ventricular sense line 49. The microprocessor 19 may be programmed to respond to such a signal by generating skeletal muscle stimulation. Alternatively, in the event that the patient's natural heart rate falls below a predetermined rate, then the microprocessor will send an atrial pace control signal on line 46, a ventricular pace control signal on line 50, or both signals, to the pacemaker 17 to generate a pacing pulse to the heart. In addition, the microprocessor 19, may be programmed to trigger skeletal muscle stimulation after such a pacing event. Programming of synchronous operation of the skeletal muscle stimulator includes the specification of a synchronization ratio which determines the ratio of cardiac events for each skeletal muscle stimulation burst. The microprocessor 19 resets a cardiac event counter with each initiation of a skeletal muscle stimulation burst and increments the counter with each subsequent cardiac event. For each skeletal muscle stimulation burst, the microprocessor 19 waits a predetermined and programmed delay interval before initiating the burst.

Other programmed parameters which may beutilized are an interpulse interval (the time between sequential pulses), the stimulus duration, the recharge duration, the cross-channel blanking duration and a maximum muscle stimulation rate. All or some of these parameters may have preprogrammed sets of values which depend on the rate at which the heart is beating. An interpulse interval determines the time intervals between each individual pulse within a burst of pulses. A burst frequency is the reciprocal of the interpulse interval. The maximum muscle stimulation rate is an upper rate boundary of synchronization of cardiac and muscle stimulation activity. Upon a cardiac event occurring at cardiac rates faster than the maximum muscle stimulation rate, the microprocessor will fail to generate skeletal muscle stimulation but will, instead, stimulate the skeletal muscle based upon triggering by the next subsequent cardiac event.

The antiarrhythmia pacemaker of the present invention monitors activity of the heart to determine when and how to deliver an antiarrhythmia therapy. The flow chart of FIG. 6 defines one example of arrhythmia detection, confirmation and classification operations, performed by a microprocessor, which may be employed by the antiarrhythmia pacemaker of the present invention. The microprocessor 19 of FIG. 1 is programmed to respond to atrial sense signals on line 45 and ventricular sense signals on line 49 from the pacemaker 17. For some or all cardiac cycles, the microprocessor may measure a time interval associated with that cardiac cycle. The program in the microprocessor may define a cardiac cycle as an atrial cycle interval (P wave to P wave) or a ventricular cycle interval (R wave to R wave). Furthermore, interval timing may relate to stimulated cardiac events as well as to intrinsic cardiac events.

Figure 6:
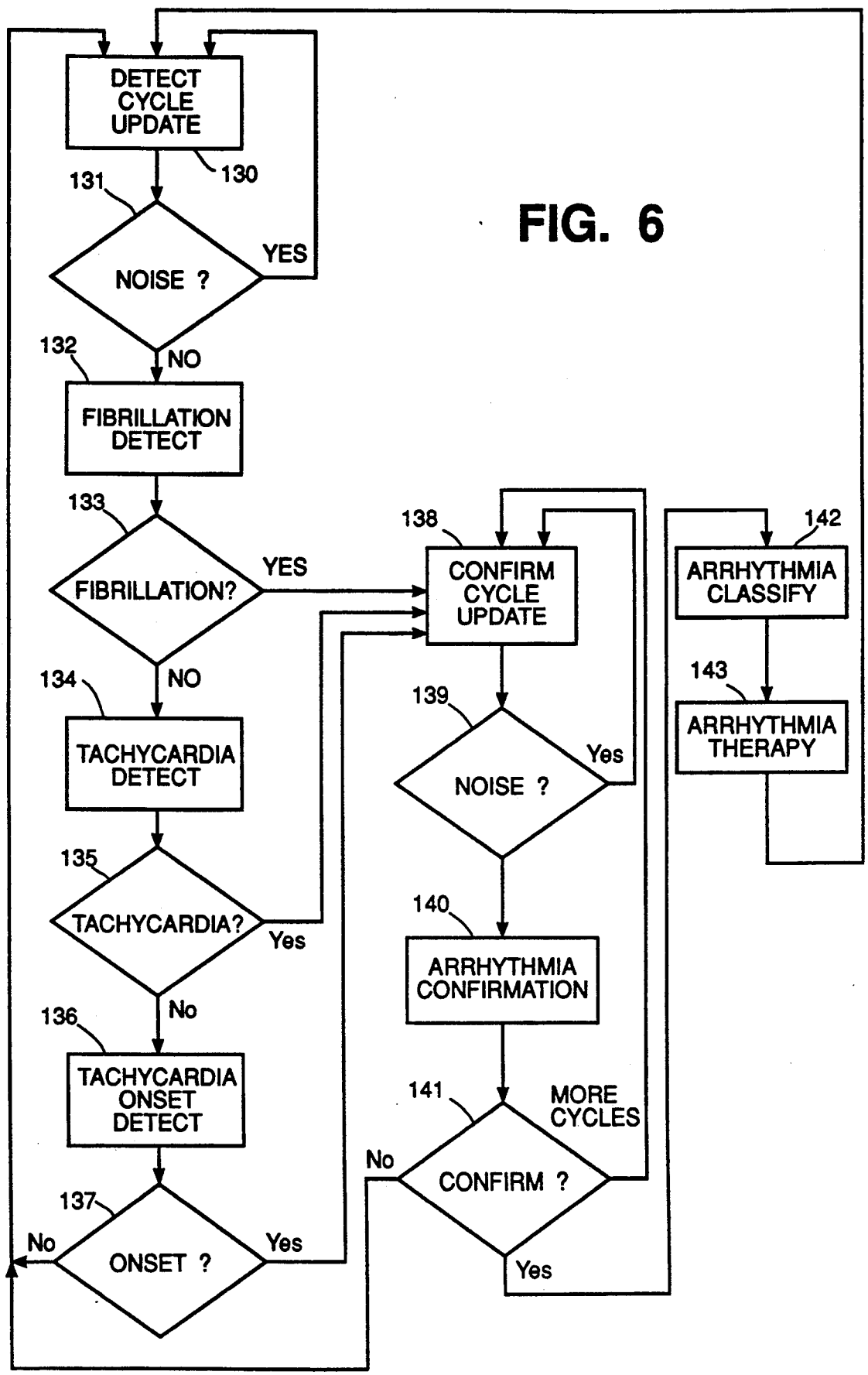
FIG. 6 is a flow chart setting forth the operations of arrhythmia detection, confirmation and classification.

Referring to FIG. 6, microprocessor 19 first performs arrhythmia detection. In a detect cycle update 130 operation, the microprocessor measures the time interval associated with the present cardiac cycle. The microprocessor may discard interval information for a particular cardiac cycle based on the duration of an interval so as to ignore signals due to noise or artifacts, as controlled by the detect cycle noise 131 logic operation. The resulting interval information as well as a log of information concerning the recent history of interval information is stored by the microprocessor in RAM memory 121 (FIG. 1) and used to detect, confirm and classify arrhythmias. During arrhythmia detection, unless a cardiac cycle is characterized as a noise cycle, each time the microprocessor updates the interval duration and interval history memories in block 130, it begins to perform arrhythmia detection beginning with fibrillation detection 132 operation. Fibrillation detection 132 operation distinguishes tachyarrhythmias with very short intervals by comparing the current interval duration to a predetermined short interval, called a fibrillation detection interval, which is considered to be indicative of fibrillation (for example, 250 msec). However, the microprocessor does not detect an arrhythmia based on only one cardiac cycle. Instead, an X out of Y detection criterion is used to define an arrhythmia, in which a criterion is met only when at least X of the last Y cardiac cycles have cycle intervals shorter than the defined interval. For example, fibrillation detection may require that 8 of the last 10 intervals be shorter than 250 msec. If so, a fibrillation detect 133 logic operation initiates arrhythmia confirmation, beginning with a confirm cycle update 138 operation. If not, the microprocessor performs a tachycardia detection 134 operation.

Tachycardia detection 134 operation discerns tachycardias in the same manner as fibrillation detection 132 operation described above, by comparing the current cardiac cycle length with a predetermined limit and by monitoring the history of cardiac cycle lengths with respect to this comparison. The cycle length limit is called a tachycardia detection interval. It is programmable to a duration ranging from 200 to 600 msec. The X of Y detection criterion for tachycardia detection is also programmable. Common criteria may be 8 out of 10, 12 out of 15 or 16 out of 20. If the X of Y criterion is met, a tachycardia detect 135 logic operation initiates arrhythmia confirmation, beginning with the confirm cycle update 138 operation. If not, the microprocessor performs a tachycardia onset detection 136 operation.

Tachycardia onset detection 136 operation recognizes a sudden and sustained decrease in interval duration to indicate the onset of a tachycardia episode. It incorporates two detection methods, the X of Y criterion to ensure that the decrease in interval length is sustained and a change of interval detector which checks for a sudden change in interval length. The change of interval detector employs a predetermined and programmable delta function. Delta is the amount by which the intervals must decrease at onset to satisfy the change of interval detector. The cycle length limit is programmable and called an onset detection interval. The range of onset detection intervals is, like the tachycardia detection interval, from 200 to 600 msec. However, the onset detection interval must be programmed to an interval length longer than the tachycardia detection interval. The X of Y detection criterion for tachycardia onset detection is also programmable.

The detect cycle update 130 operation performs two averaging operations for usage by the change of interval detector. When the cardiac rhythm is stable and slow, detect cycle update averages cardiac cycle intervals to obtain a normal sinus rhythm interval. This averaging occurs when cardiac cycle intervals are longer than the onset detection interval for more than a predetermined number of consecutive cardiac cycles. The detect cycle update 130 operation also performs a short-term average of a predetermined number of the most recent cardiac cycles (for example, 2 cycles). The tachycardia onset detector 136, discerns a change of interval when the short-term average interval is shorter than the normal sinus rhythm interval less the predetermined and programmed delta interval. If the change of interval and onset X of Y criterion is met, an onset detect 137 logic operation initiates arrhythmia confirmation, beginning with the confirm cycle update 138 operation. If not, the microprocessor has not detected an arrhythmia and operation control returns to the detect cycle update 130 operation.

The confirm cycle update 138 operation is analogous to the detect cycle update 130 operation. The microprocessor measures the time interval associated with the present cardiac cycle, discards interval information for noisy cardiac cycles (under the control of the confirm cycle noise 139 logic operation), and logs interval length and interval length history information.

An arrhythmia confirmation 140 operation confirms the presence of a tachyarrhythmia before delivering an antitachycardia pacing, cardioversion or defibrillation therapy. Like the arrhythmia detection operations 132, 134 and 136, arrhythmia confirmation uses an X out of Y criterion which compares a history of intervals compiled in the confirmation cycle update 138 operation with respect to a tachycardia confirmation interval. The value of the tachycardia confirmation interval depends on the arrhythmia detector which determined the presence of an arrhythmia. If the arrhythmia was detected by the tachycardia onset detector, the tachycardia confirmation interval is set to the normal sinus rhythm interval determined by the detect cycle update 130 operation less one-half the predetermined and programmed delta interval. If the arrhythmia was detected by the fibrillation or tachycardia detector, the tachycardia confirmation interval is set to the tachycardia detection interval. The X out of Y criterion is predetermined and may be programmed. In a confirmation logic 141 operation, if the X out of Y criterion is met, the pacemaker performs an arrhythmia classification 14 operation. If the criterion is not met, the pacemaker again monitors for arrhythmia detection in the detect cycle update 130 operation. If more cycles are required to determine whether the X of Y criterion is met, control returns to the confirm cycle update 138 operation.

After confirmation of tachyarrhythmia and before delivering therapy, the arrhythmia classification 142 operation classifies the tachyarrhythmia to determine the therapy or therapies to be used in treating the tachyarrhythmia. Classification is based on an X out of Y criterion applied to the cardiac cycle intervals which were monitored in confirmation cycle update 138 operation. These cycle intervals are compared to two predetermined and programmable intervals—a minimum tachycardia cycle length for antitachycardia pacing ($MinTCL_{BUQ}$) and a maximum tachycardia cycle length for defibrillation ($MaxTCL_{egjc}$). For arrhythmias with detected intervals shorter than $MinTCL_{BUQ}$, antitachycardia pacing is ineffective. For arrhythmias with detected intervals shorter than $MaxTCL_{egjc}$, that patient is considered to be hemodynamically compromised by the arrhythmia and therefore requires defibrillation shock therapy. So if the detected intervals are longer than $MinTCL_{BUQ}$, the microprocessor initiates antitachycardia pacing in an arrhythmia therapy 143 operation. (Note that arrhythmia has been confirmed at this point.) If the detected intervals are shorter than $MinTCL_{BUQ}$ but longer than $MaxTCL_{egjc}$, the microprocessor initiates antitachycardia pacing in the arrhythmia therapy 143 operation, but will also use defibrillation if antitachycardia pacing is not successful. If the detected intervals are shorter than $MaxTCL_{egjc}$, then the microprocessor initiates defibrillation in the arrhythmia therapy 143 operation. The arrhythmia therapy 143 operation is discussed in detail hereinafter. Following the arrhythmia therapy 143 operation, the pacemaker returns to arrhythmia detection operation in detect cycle update block 130.

Other embodiments of the antitachycardia pacemaker of the present invention may employ other means for detecting the occurrence of arrhythmia episodes, some of which involve the usage of physiological and metabolic sensors. In this regard, reference may be made to U.S. patent application Ser. No. 654,930, entitled "APPARATUS AND METHOD FOR DETECTING ABNORMAL CARDIAC RHYTHMS IN DUAL CHAMBER ARRHYTHMIA CONTROL SYSTEM", filed on Feb. 13, 1991, in the names of Tibor A. Nappholz et al., and to U.S. patent application Ser. No. 665,842, entitled "APPARATUS AND METHOD FOR DETECTING ABNORMAL CARDIAC RHYTHMS USING AN ULTRASOUND SENSOR IN AN ARRHYTHMIA CONTROL SYSTEM", filed on Mar. 8, 1991, in the names of Tibor A. Nappholz et al., both of which are assigned to the assignee of the present invention. Reference may also be made to U.S. patent application Ser. No. 667,316, entitled "APPARATUS AND METHOD FOR DETECTING ABNORMAL CARDIAC RHYTHMS USING EVOKED POTENTIAL MEASUREMENTS IN AN ARRHYTHMIA CONTROL SYSTEM", filed on Mar. 8, 1991, by Tibor A. Nappholz et al., and to U.S. patent application Ser. No. 738,184, entitled "DETECTION OF CARDIAC ARRHYTHMIAS USING CORRELATION OF CARDIAC ELECTRICAL SIGNALS AND TEMPORAL DATA COMPRESSION", filed on Jul. 29, 1991, by Bruce M. Steinhaus et al., both of which are assigned to the assignee of the present invention.

In addition to performing an antiarrhythmia therapy in response to the detection of arrhythmias, the antiarrhythmia pacemaker of the present invention also performs a therapy upon the detection of arrhythmia precursors.

Figure 7A:
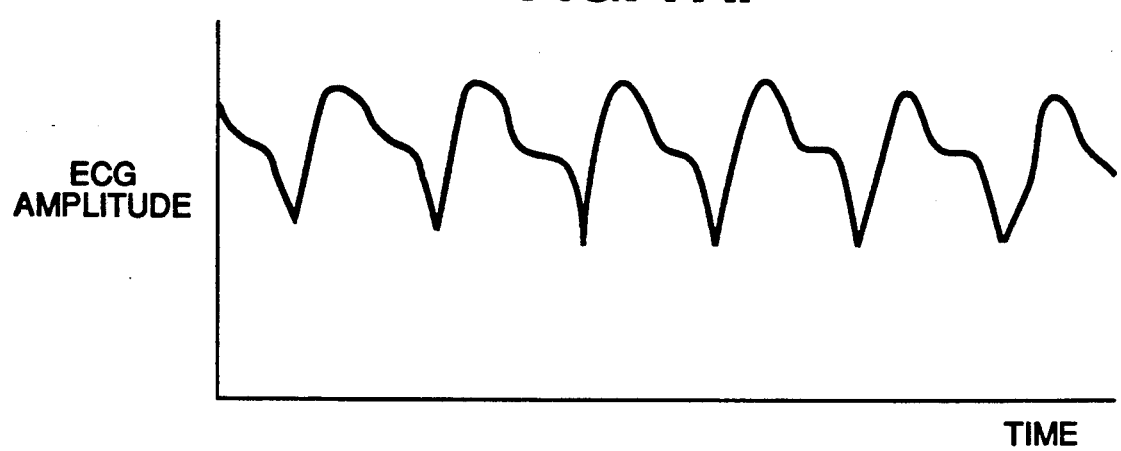
FIGS. 7A-7C are illustrations of sample electrocardiograms (ECGs) showing abnormal cardiac rhythms recognized as precursors to malignant cardiac arrhythmias, including ventricular tachycardia (FIG. 7A), ventricular couplets (FIG. 7B) and premature ventricular complexes (FIG. 7C), detected by an antiarrhythmia pacemaker of the present invention.
Figure 7B:
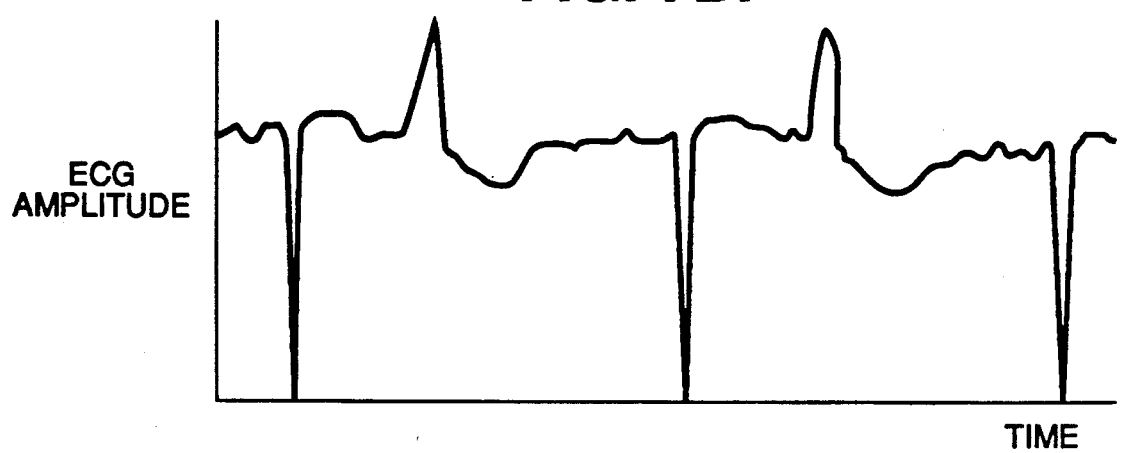
Figure 7C:
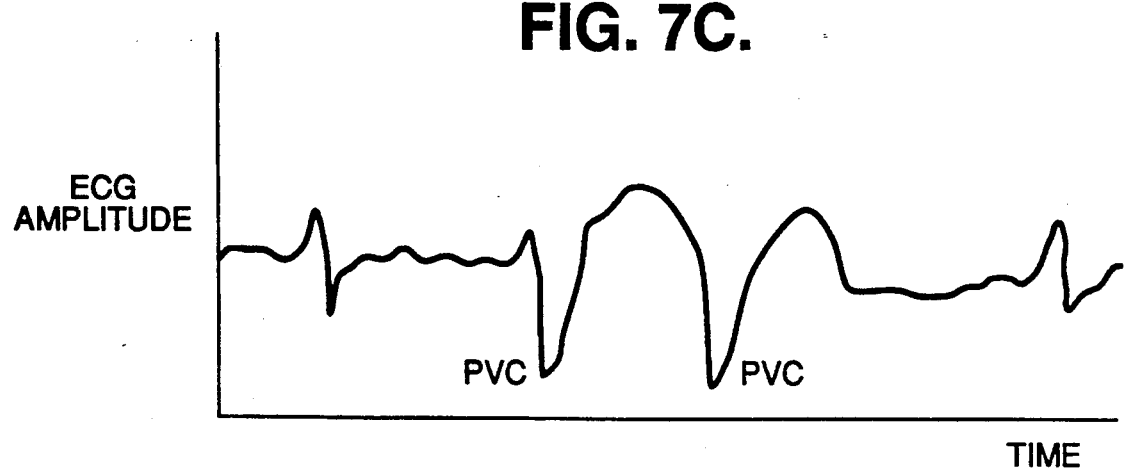

The pacemaker 17 of FIG. 1 acquires intracardiac electrogram (IEGM) samples which the microprocessor 19 monitors and analyzes to detect arrhythmia precursors. Some IEGM features are known to occur in patients experiencing potentially lethal ventricular tachyarrhythmias. Two types of precursors have been identified which are antecedent to ventricular fibrillation or sudden death relating to: (a) abnormal ventricular rhythms, and (b) abnormal electrocardiogram polarization waveforms. FIGS. 7A-7C illustrate ventricular fibrillation precursors displaying abnormal ventricular rhythms in the form of complex ventricular arrhythmias, including ventricular tachycardia (FIG. 7A), ventricular couplets (FIG. 7B) and premature ventricular complexes (PVCs in FIG. 7C). The degree of complexity of such ventricular arrhythmias (for example, dynamic oscillations in the rate of emergence of ventricular tachycardia or wild variations in the length of ventricular tachycardia outbursts) and an increasing rate of occurrence of ventricular arrhythmias are as important as the presence of such features in the detection of precursors. Density of ventricular arrhythmias, defined as the ratio of abnormal to normal ventricular rhythms, is also helpful for diagnosing harmful arrhythmias.

Precursors which are characterized primarily by abnormalities in the IEGM waveform, rather than by abnormalities in cardiac rate or rhythm, are shown in FIGS. 8A, 8B and 9A-9C and include: repolarization abnormalities, ST-segment changes and late potentials. The microprocessor must analyze fine detail within the IEGM waveforms to detect waveform abnormality precursors. The microprocessor 19 analyzes the fine detail of IEGMs to detect R-on-T ventricular premature depolarizations (FIG. 8A) which frequently initiate malignant arrhythmias, repolarization abnormalities such as a prolonged QT intervals (FIG. 8B), and ST-segment changes (FIGS. 9A and 9B, ST-segment elevation and depression). All these events have diagnostic significance for predicting imminent ventricular fibrillation. Late potentials (designated LP in FIG. 9C) also anticipate episodes of ventricular tachycardia or fibrillation.

Timing of particular precursors, as well as their presence, is diagnostically important for determining onset and risk of sudden death. In many cases of sudden cardiac death, the first indications of arrhythmia are a maximum incidence of intermediately frequent (from 100 to 500 per hour) premature ventricular complexes occurring between fifteen and six hours prior to ventricular fibrillation. This is followed by an increased frequency in ventricular couplets and runs of complex ventricular arrhythmias, including ventricular tachycardia. Repolarization abnormalities often appear in the IEGM waveform several hours before ventricular fibrillation. Often there is an increased incidence of ST-segment changes having an amplitude greater than 2 mm throughout the risk period and lasting until hours prior to sudden death. Within the three hours prior to sudden death, ST-segment changes of this amplitude diminish in incidence. In the final six hours preceding sudden death there is an increased incidence of lower amplitude ST-segment changes. During these final hours the ST-segment change gradually diminishes from a high amplitude toward the baseline.

The microprocessor 19 constantly acquires IEGM signals and from these detects ventricular events and analyzes the fine detail of portions of the signal using known analytical techniques. Much of the diagnostic detail of an IEGM lies in the vicinity of the QRS-complex. FIG. 10 illustrates a waveform of a normal cardiac cycle with conventional timing intervals indicated therein. S-T and Q-T intervals end, respectively, at the beginning and end of the T wave. Normal P waves have a duration ranging from 0.04 to 0.08 seconds and precede the R wave (the P-R interval) by from 0.12 to 0.20 seconds. The normal duration of a QRS-complex is 0.04 to 0.10 sec.

Figure 11:
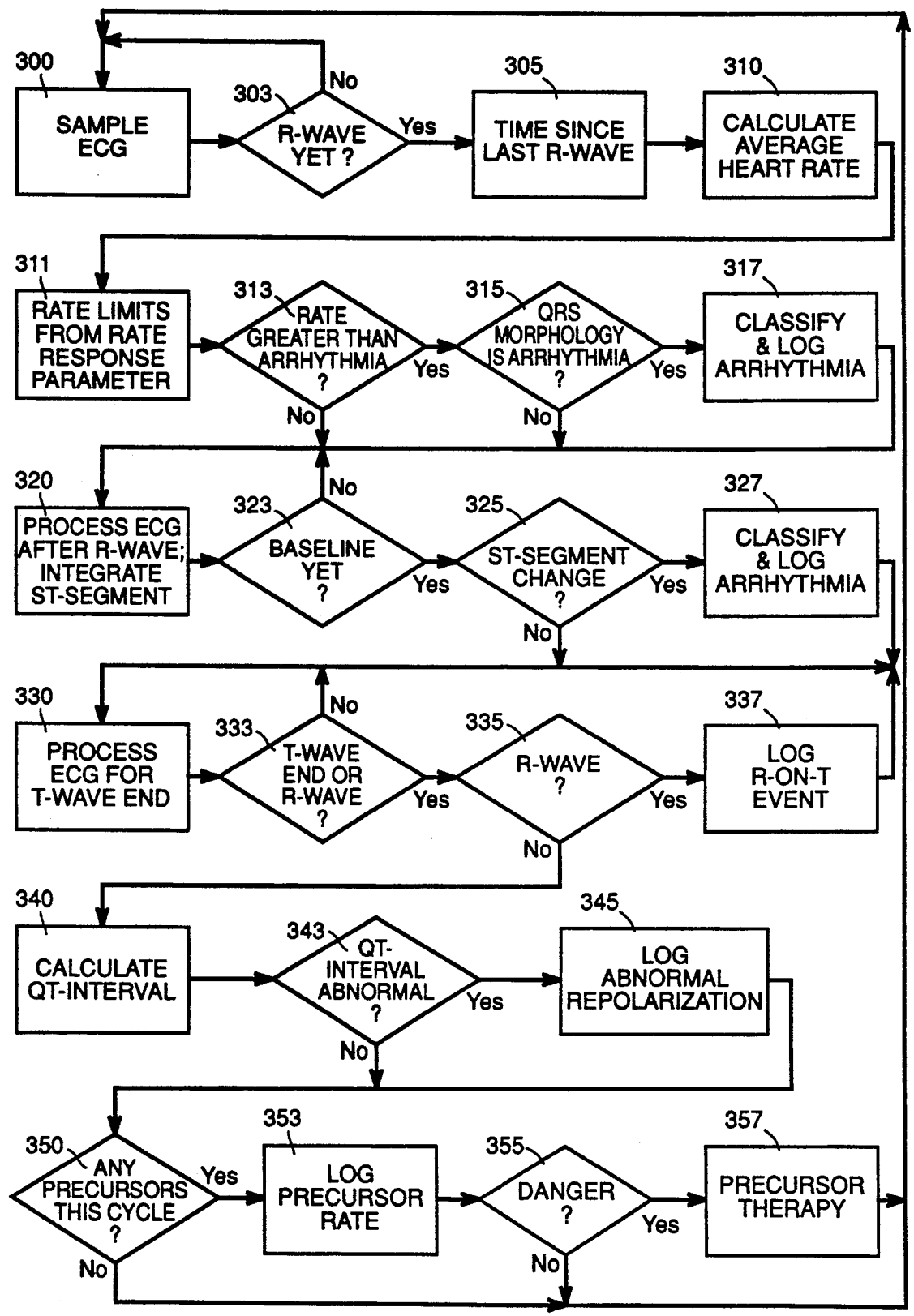
FIG. 11 is a flow diagram illustrating the method performed by an antiarrhythmia pacemaker of the present invention for detecting precursors of malignant cardiac arrhythmias.

For each cardiac cycle, the microprocessor 19 performs the operations shown in the flow diagram of FIG. 11. The microprocessor identifies cardiac events, correlates the events with time intervals within the cardiac cycle, and analyzes the detailed structure within the IEGM. The microprocessor first searches IEGM signals for the R wave within the present cardiac cycle in block 303. The R wave normally has the largest slope within the cardiac cycle (the greatest change in polarization amplitude in a short time) and a large amplitude. The preferred embodiment of the invention uses a delta comparator, a slope detector, to detect R waves. The microprocessor continuously samples in block 300 until it detects an R wave in block 303. As part of the sampling process in block 300, the microprocessor saves data relating to morphology of the QRS-complex for further analysis. This data may include samples of IEGM amplitude, maximum positive and negative polarity excursions and derivatives (slopes) of the leading and trailing edge of the QRS-complex. After detecting the R wave, the microprocessor determines the elapsed time since the last R wave in block 305. The reciprocal of the elapsed time is the instantaneous heart rate for the present cycle. The microprocessor calculates this reciprocal value and averages the instantaneous rate over a few cardiac cycles (for example, four) to determine the average rate in block 310. In block 313, the microprocessor compares the current average rate to predetermined limit values. These limit reflect the rates of various types of arrhythmias. The limits may vary, depending on certain physiological characteristics, indicative of exercise, for example. Standard rate-responsive sensors may be used for this purpose. Therefore, before the test in block 313, the rate limits are set in block 311 in accordance with whichever standard rate-response parameter is monitored.

If the average rate lies within the boundaries set for a particular class of ventricular arrhythmia in block 313, the microprocessor (in block 315) tests the morphology of details within the QRS-complex against predetermined and stored morphology parameters to classify the rhythm as either an arrhythmia or a normal rhythm. If the microprocessor detects an arrhythmia, it classifies the arrhythmia according to type and logs the occurrence of the particular arrhythmia type in memory in block 317.

In block 320 the microprocessor processes subsequent samples and analyzes the IEGM signal from the R wave to the T wave to determine the QT interval and to diagnose myocardial ischemia from ST-segment morphology. The ST-segment occurs in the sampling window beginning at the J-point following a QRS-complex as is known in the art (see FIG. 10) and persists for at least 80 milliseconds. ST-segment depression, defined as a horizontal or downsloping shift of 0.1 mV (some researchers use 0.2 mV or 0.3 mV) during the ST-segment which endures for at least 30 seconds in consecutive heartbeats (some researchers use from 40 to 60 seconds), correlates positively with myocardial ischemia both in exercise tolerance tests and in ambulatory testing of resting patients and patients performing daily activities. Most patients with stable angina and proven coronary artery disease frequently have episodes of ST-segment depression during daily life. ST-segment changes warn of injury to myocardial tissue even in patients afflicted with otherwise asymptomatic silent myocardial ischemia, since they are frequently accompanied by regional disturbances of myocardial perfusion and disturbances of left ventricular function. The microprocessor analyzes the waveform to determine when the T wave occurs (it should arrive within 400 milliseconds of the R wave) within the current cardiac cycle. After detecting the R wave, the microprocessor may change the acquisition parameters of the IEGM signal (for example, by selecting a different set of impedances in an input amplifier to adjust the bandwidth) to better analyze the waveform structure following the R wave.

Referring back to FIG. 10, immediately after the comparator detects an R wave, the microprocessor 19 processes the IEGM to measure the leading and trailing R wave slopes, then continues to track the signal down the S wave and back up until the slope diminishes at what is called the J-point. While processing the IEGM (in block 320 of FIG. 11) from the J-point until the waveform crosses the baseline (tested in block 323), the microprocessor integrates and determines the slope of the signal. If the magnitude (the absolute value) of the integrated signal is larger than at least one predetermined value and remains larger for a consecutive number of cardiac cycles lasting a predetermined time (for example, 40 seconds), then the microprocessor classifies this event as an ST-segment elevation. If the integrated signal is below the baseline (a negative signal) and the slope is level or negative, then the microprocessor classifies the event as ST-segment depression, an indication of ischemia. If the ST-segment is either elevated or depressed by a value greater than a predetermined value (block 325 of FIG. 11) the microprocessor stores a code in memory to identify this incidence in block 327. If the ST-segment is abnormal, either depressed or elevated, the microprocessor may use the total duration of deviation persistence as an index of ischemia.

Figure 9A:
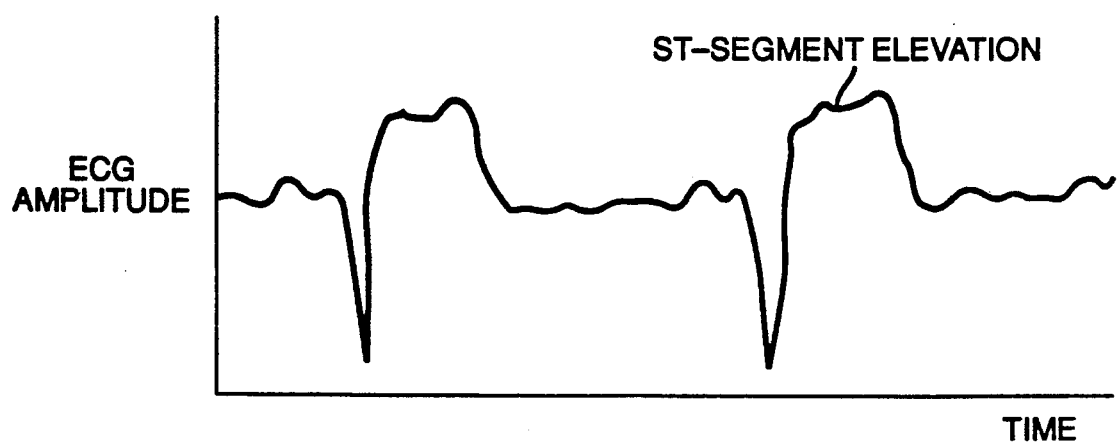
FIGS. 9A-9C are additional illustrations of samples of the detailed morphology of ECGs which are recognized as precursors to malignant cardiac arrhythmias, including ST-segment elevation (FIG. 9A), ST-segment depression (FIG. 9B) and late potentials (FIG. 9C), detected by an antiarrhythmia pacemaker of the present invention.
Figure 9B:
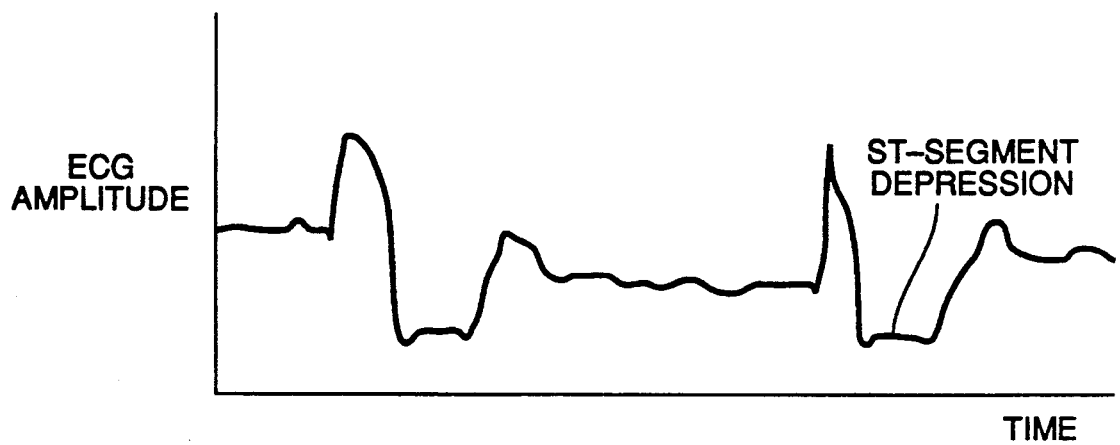
Figure 9C:
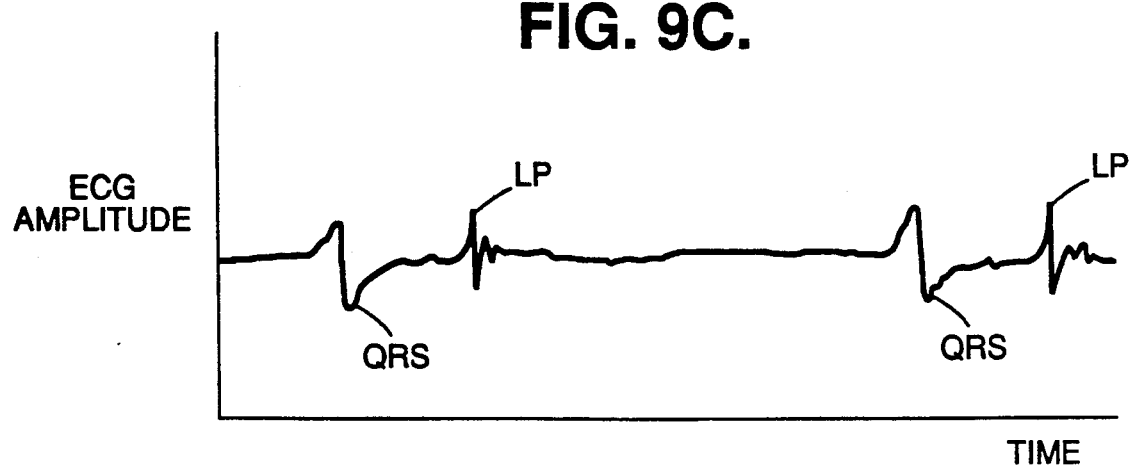

Also in block 320, while processing the IEGM following the QRS-complex, the microprocessor 19 analyzes the data to determine the presence, amplitude, frequency content and duration of late potentials (FIG. 9C). The presence of late potentials predicts subsequent episodes of ventricular tachycardia, possibly leading to ventricular fibrillation and sudden cardiac death. Late potentials are fluctuations in IEGM signal amplitude occurring more than 10 milliseconds after the QRS-complex. The amplitude, frequency content and duration of the late potential are diagnostically significant for predicting the occurrence of ventricular tachycardia and ventricular fibrillation. In an operation distinct from the ST-segment processing, the microprocessor analyzes the samples beginning about 10 milliseconds following the end of the QRS-complex and persisting for up to 125 milliseconds. In the preferred embodiment of the invention this analysis may include: (1) determining the peak positive and negative deflections of the signal from the baseline amplitude, (2) detecting the presence and duration of the late potential by detecting the first (if any) and last samples wherein the deflection from baseline is greater than a predetermined amplitude within the late potential window, (3) averaging the late potential signal for the present cardiac cycle with that of previous cycles beginning with the first sample having an amplitude greater than the predetermined trigger amplitude, and (4) performing Fourier analysis of the data within the late potential sample window. If the late potential is present and has an amplitude greater than a predetermined level, the microprocessor logs a code signifying the presence of the late potential as well as the amplitude, duration and one or more parameters specifying frequency content information in block 327 of FIG. 11.

In block 330 the microprocessor 19 continues to process the IEGM to detect the end of the T wave or the occurrence of an R wave (block 333). If the next R wave occurs during the T wave (block 335), the microprocessor notes this abnormality and stores a code in memory reflecting the incidence of an R-on-T beat in block 337. At the end of the T wave in block 340 the microprocessor determines the QT-interval illustrated in FIG. 10. In block 340, the microprocessor normalizes the QT-interval to cardiac cycle time (R-R) in accordance with standard techniques. In block 343, the microprocessor compares the normalized QT-interval with a predetermined threshold QT-interval value to detect abnormalities in repolarization (see FIG. 8B). If an abnormality occurs the microprocessor stores a code to signify the event in block 345.

The microprocessor 19 may designate a separate circular buffer for each of the precursor events (ventricular arrhythmia, a particular type of ventricular arrhythmia, ST-segment changes, and repolarization) or it may tag each type of precursor with an identifying code and store it in a single circular buffer. Upon the identification of any of the precursors (block 350), the microprocessor will also update a similar circular buffer memory (block 353) to store the rate of precursor occurrences of any type. If, upon updating the precursor rate buffer, the microprocessor detects a rate greater than a predetermined value or otherwise flags a dangerous situation (block 355), the microprocessor will update a warning memory and may initiate a precursor therapy in block 357, as will be described hereinafter.

The therapy performed in arrhythmia therapy 143 operation of FIG. 6 and precursor therapy 357 operation of FIG. 11 is a combination of arrhythmia pacing stimulation, applied to the heart, and a therapy for ameliorating myocardial ischemia by stimulating contraction of a skeletal muscle graft. The first symptom of a ventricular arrhythmia is frequently an episode of myocardial ischemia, a severe reduction of coronary flow, in which the supply of oxygen to the myocardium is inadequate to meet the oxygen demands of the tissue.

One type of ischemia, supply ischemia, is a failure of myocardial contractility caused by a lack of blood flow to the myocardium due to complete cardiac occlusion. Degradation of myocardial contractility causes systolic failure, which further aggravates the ischemia condition by lowering cardiac output, and may also result in diastolic dysfunction, which precipitates pulmonary congestion and shortness of breath. The antiarrhythmia pacemaker of the present invention, upon detecting either an arrhythmia or an arrhythmia precursor, initiates skeletal muscle graft stimulation, or changes the control parameters of such stimulation, to increase cardiac output, thereby assisting myocardial perfusion.

A second type of ischemia, demand ischemia, is a narrowing, but not total occlusion, of the coronary arteries, combined with an increase of oxygen demand that occurs when the heart rate is increased during pacing-induced angina. Rather than a systolic failure, demand ischemia is predominantly a diastolic dysfunction in which pulmonary congestion results from impaired return of blood from the lungs to the left side of the heart. In the case of demand ischemia, the antiarrhythmia pacemaker of the present invention increases blood flow to the heart to alleviate damage to the heart muscle from ischemia.

The initial stage of myocardial ischemia, angina pectoris, is reversible. Prolonged ischemia causes irreversible physiological changes, including cell death and necrosis (myocardial infarction). Ischemia may cause death in case of a severe flow reduction to less than 20% of normal flow for more than 30 to 45 minutes or if slightly less flow reduction up to 40% of normal occurs for more than a few hours. Prolonged ischemia may progress to irreversible infarction. The antiarrhythmia pacemaker of the present invention is intended to act quickly, at the first detection and confirmation of an arrhythmia (block 143 of FIG. 6), or earlier, at the first detection of an arrhythmia precursor (block 357 of FIG. 11) to terminate the effects of myocardial ischemia in its reversible stage.

A critical consequence of ischemia is its propensity to degenerate into ventricular arrhythmias and sudden death by the following mechanisms. Ischemia induces ventricular automaticity in which multiple ventricular ectopic beats occur in rapid succession. A ventricular tachycardia then occurs in which there is insufficient time for diastolic filling. Cardiac output declines, further aggravating ischemia and leading to the risk of acute myocardial ischemia. In this manner, ischemia predisposes the heart to development of totally disorganized ventricular rhythm called ventricular fibrillation. Regular cardiac pumping ceases and sudden cardiac death develops. The sole treatment for this condition is defibrillation. The arrhythmia pacemaker of the present invention applies a combined therapy, usually prior to ventricular fibrillation, comprised of arrhythmia pacing stimulation and muscle graft stimulation to terminate an arrhythmia while stimulating the muscle graft to increase perfusion of the heart. The pacemaker applies the therapy at the first sign of arrhythmia, at the precursor, tachycardia or fibrillation stages. If the arrhythmia changes form, such as from precursor to tachycardia or tachycardia to fibrillation, the pacemaker may alter the therapy to best terminate the abnormal cardiac condition.

Two coronary arteries, which arise from the aorta immediately above the semilunar valves, supply the heart with blood. Blood is fed to the heart throughout the cardiac cycle, under the force of lateral aortic pressure. Branches of the coronary arteries penetrate the cardiac muscle to supply deeper layers of the heart where intravascular pressure becomes progressively lower more peripherally from the aorta. The antiarrhythmia pacemaker of the present invention provides for skeletal muscle graft stimulation to increase cardiac output and lateral aortic pressure during an ischemia episode, raising blood pressure throughout the coronary circulation to reduce cardiac occlusion and increase perfusion of the heart.

Detection and confirmation of an occurrence of a cardiac abnormality, either an arrhythmia precursor, tachycardia or fibrillation, is evidence of diminished myocardial perfusion. Thus, in addition to performing an antiarrhythmia pacing therapy, the pacemaker in the arrhythmia therapy 143 operation of FIG. 6, directs the generation of stimulation pulses to the skeletal muscle graft to increase cardiac output, lateral aortic blood pressure and coronary arterial perfusion. These stimulation pulses are in the form of repetitive, brief bursts of pulses. Upon a triggering event, a sensed intrinsic cardiac event or a cardiac pacing pulse stimulus delivery, the pacemaker waits a predetermined delay time then generates the burst of pulses to stimulate contraction of the skeletal muscle graft.

In the preferred embodiment of the invention, the skeletal muscle stimulation pulse amplitude varies from 3 to 12 volts. The predetermined pulse width ranges from 0.01 to 2 milliseconds.

Figure 12A:
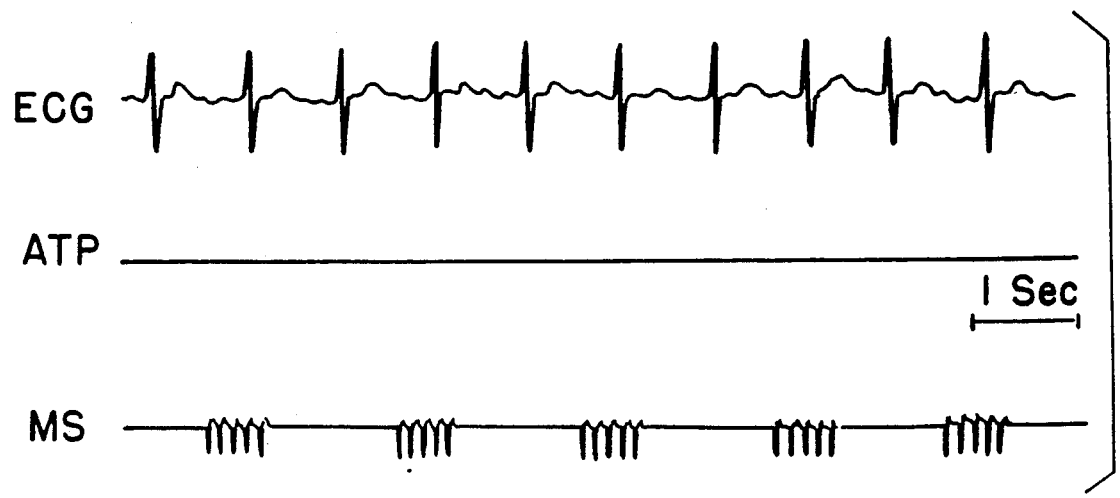

FIG. 12A depicts signals for an electrocardiogram (ECG), an antitachycardia pacing stimulation (ATP) and a skeletal muscle stimulation (MS), when the heart is functioning with a normal sinus rhythm. The electrocardiogram (ECG) illustrates natural electrical activity of the heart which inhibits operation of cardiac pacing stimulation. Because the heart is functioning with a normal sinus rhythm, the pacemaker is not generating an antiarrhythmia pacing stimulation (ATP) to stimulate the heart. In this example, skeletal muscle stimulation (MS) generates a burst of pulses for one out of every two natural cardiac contractions to assist the heart and increase cardiac output.

Figure 12B:
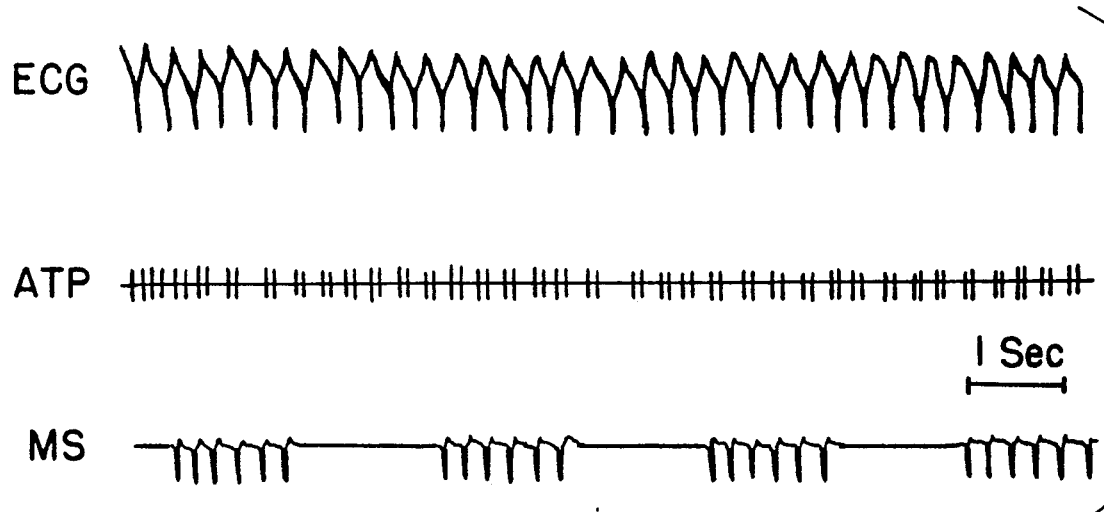

FIG. 12B depicts signals for an electrocardiogram (ECG), an antitachycardia pacing stimulation (ATP) and a skeletal muscle stimulation (MS), when the heart is functioning under ventricular tachycardia conditions. The pacemaker generates an antitachycardia pacing therapy (ATP), which is intended to terminate the tachycardia episode. This example of antitachycardia pacing is disclosed in U.S. Pat. No. 4,390,021 invented by R. A. J. Spurrell et al., issued Jun. 28, 1983, entitled "Two Pulse Tachycardia Control Pacer". This patent discloses a pacemaker for controlling tachycardia in which the coupled interval, as well as the initial delay, is scanned. The time parameters which are successful in terminating the tachycardia are stored so that upon confirmation of another tachycardia event, the previously successful time parameters are first attempted.

The pacemaker generates skeletal muscle stimulation (MS) in the form of a burst of pulses for no more than one out of every two natural cardiac contractions. If the natural cardiac interval is shorter than a predetermined arrhythmia interval limit, the pacemaker skips a cardiac cycle and does not generate a burst of pulses until the next cardiac cycle occurs in which the interval between bursts is not shorter than the limit. The pacemaker may set the muscle stimulation pulse amplitude and duration to new predetermined levels to strengthen the skeletal muscle contraction and increase cardiac output during tachycardia conditions. FIG. 12B illustrates an increased skeletal muscle stimulation pulse amplitude when tachycardia conditions are detected. In addition, the pacemaker may cause burst scanning, in which the interval between pulses within a burst shorten or lengthen to change the contraction strength of the skeletal muscle. FIG. 12B illustrates burst scanning in which the interval between pulses is lengthened with each succeeding pulse.

The pacemaker, in response to detecting and confirming a tachycardia condition, generates muscle stimulating pulse trains which remain in synchrony with the timing of heart contractions but are generated for fewer of the sensed cardiac cycles so that the interval between successive muscle stimulation pulse trains is greater than the detected tachycardia cycle interval. In the example of FIG. 12B, the interval between the pulses within the train is extended and the pulse train duration is lengthened to increase the strength of the muscle contraction.

Other examples of antitachycardia pacing techniques which appropriately augment skeletal muscle stimulation to correct a cardiac arrhythmia include the pacer disclosed in U.S. Pat. No. 3,942,534 to K. R. Allen et al., entitled Device for Terminating Tachycardia, which issued Mar. 9, 1976. Following a tachycardia detection, the pacer generates an atrial (or ventricular) stimulus after a delay interval. If that stimulus is not successful in terminating the condition, then another stimulus is generated after another premature heartbeat following a slightly different delay. The device constantly adjusts the delay interval by scanning through a predetermined delay range. Stimulation ceases as soon as the heart is restored to sinus rhythm. If successful reversion is not achieved during one complete scan, then the cycle is repeated. The device further provides a second stimulus following the first, both stimuli occurring within the tachycardia cycle, i.e. before the next naturally occurring rapid beat.

Also, U.S. Pat. No. 4,398,536 to T. A. Nappholz et al., entitled "Scanning Burst Tachycardia Control Pacer", issued Aug. 16, 1983, discloses a scanning burst tachycardia control pacer. U.S. Pat. No. 4,406,287 invented by T. A. Nappholz et al., issued Sep. 27, 1983, entitled "Variable Length Scanning Burst Tachycardia Control Pacer", discloses a variable length scanning burst tachycardia control pacer. Furthermore, U.S. Pat. No. 4,408,606 to R. A. J. Spurrell et al., entitled "Rate Related Tachycardia Control Pacer", issued Oct. 11, 1983, discloses a rate related tachycardia control pacer.

Even in the absence of an arrhythmia condition, the antiarrhythmia pacemaker of the present invention monitors cardiac activity to detect arrhythmia precursors, such as episodes of myocardial ischemia. Therefore, upon detection of an arrhythmia precursor, the microprocessor in precursor therapy 357 operation of FIG. 11 directs a therapy which augments cardiac output and lateral aortic blood pressure to improve coronary perfusion to prevent ventricular tachycardia and fibrillation by stimulating the skeletal muscle graft during acute myocardil ischaemia. This skeletal muscle stimulation therapy in response to arrhythmia precursor detection is similar to the therapy which is performed to terminate arrhythmia episodes.

The antiarrhythmia pacemaker of the present invention includes a means for stimulating a skeletal muscle graft to assist the hemodynamic status of a patient. A graft of skeletal muscle is wrapped around a patient's heart, aorta, or a compressible reservoir connected in series or parallel with the aorta. The pacemaker may be configured to perform cardiac assistance in the form of systolic augmentation or diastolic counterpulsation.

Systolic augmentation uses skeletal muscle graft stimulation to aid cardiac systole and reduce dilation due to cardiomyopathy. Stimulation of the skeletal muscle graft aids the heart by increasing cardiac output and the blood pressure within the aorta.

Diastolic counter pulsation employs skeletal muscle graft stimulation to cause aortic contraction during ventricular diastole. Relaxation of the aorta during ventricular systole helps to unload the ventricles, thereby reducing ejection impedance, cellular fatigue and peak systolic pressure, while increasing cardiac output.

Figure 13:
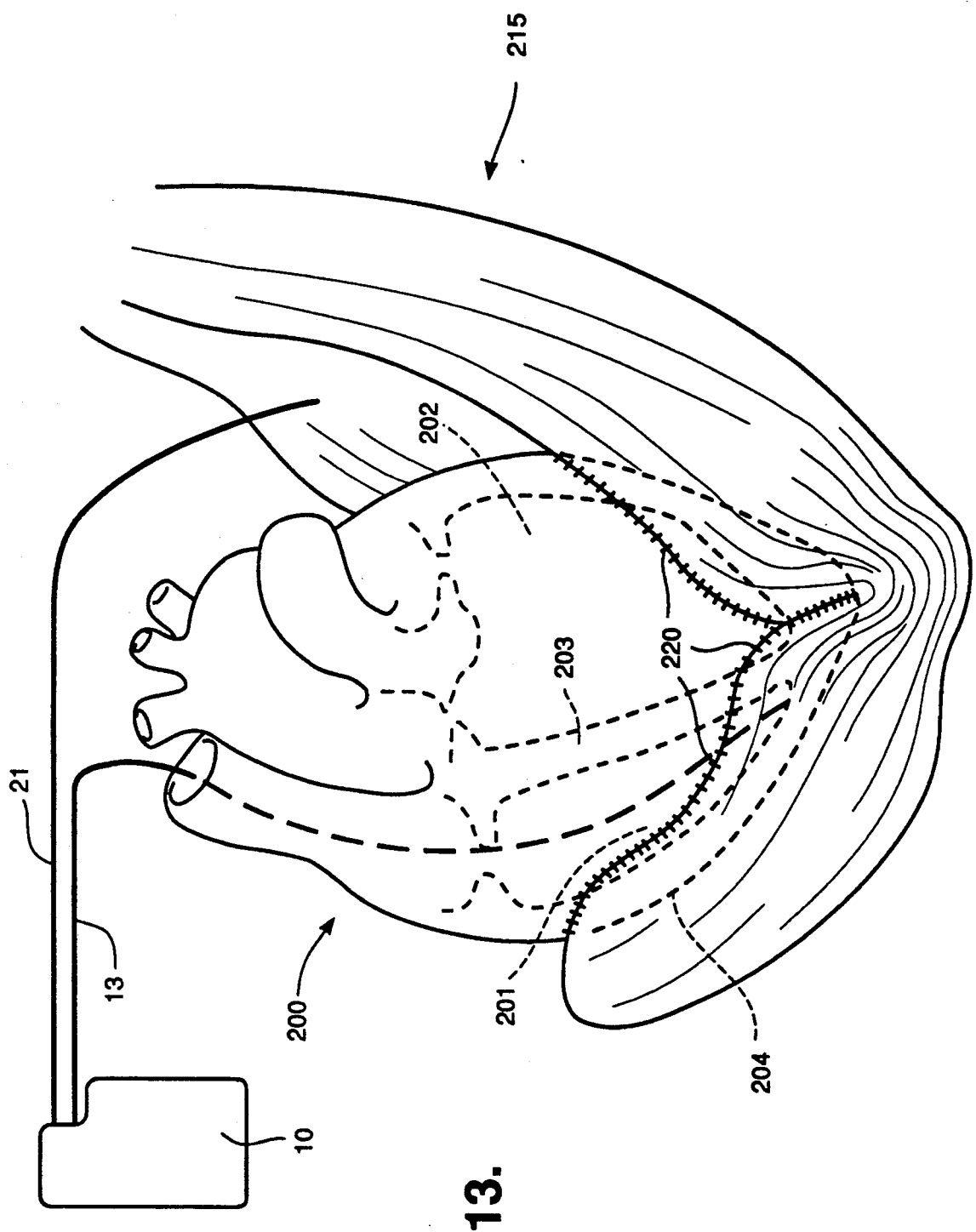
FIG. 13 illustrates one example of a cardiac assist system for performing long-term stimulation of skeletal muscles using systolic augmentation, which employs an embodiment of the antiarrhythmia pacemaker of the present invention.

FIG. 13 illustrates an example of a cardiac assist system for performing both cardiac pacing and long-term stimulation of skeletal muscles using systolic augmentation in accordance with one embodiment of the antiarrhythmia pacemaker of the present invention. A latissimus dorsi skeletal muscle graft 215 is positioned over the right ventricle 201 and left ventricle 202 of a patient's heart 200. The longitudinal fibers of the latissimus dorsi graft 215 are oriented generally parallel to the longitudinal axes of the ventricles 201 and 202 and interventricular septum 203 of the heart. The skeletal muscle is positioned in this manner so that when it is stimulated, it compresses the ventricles, particularly the left ventricle 202, and improves the force of right and left ventricular contraction. The latissimus dorsi muscle graft 215 is attached to the heart 200 along the borders of the ventricular walls 204 using running sutures 220.

A ventricular cardiac lead 13 is implanted in the heart's right ventricle 201 and a skeletal muscle lead 21 extends from the muscle stimulator 20 (of FIG. 1) to the latissimus dorsi muscle graft 215. The skeletal muscle lead 21 may be placed directly on a nerve or placed near nerve branches within the latissimus dorsi muscle graft 215 to provide for depolarization of intact motor nerve fibers.

FIG. 13 illustrates the heart/skeletal muscle configuration of a device which employs the muscle stimulation technique of systolic augmentation. The present invention is also intended to provide for cardiac assistance devices which employ the muscle stimulation technique of diastolic counterpulsation described in U.S. Pat. No. 5,009,229 to Grandjean et al, entitled "Steroid Eluting Intramuscular Lead", which issued Apr. 23, 1991.

From the foregoing discussion, it is apparent that the present invention provides an antiarrhythmia pacemaker which accomplishes substantial improvement in detecting and confirming a wide range of abnormal cardiac states and, in response to such detection and confirmation, provides a combined antiarrhythmia therapy and skeletal muscle stimulation therapy to prevent and terminate dangerous cardiac arrhythmias. The success rate of arrhythmia termination is increased while the risks of aggravating arrhythmias is decreased when the present invention is utilized. Moreover, the use of the present invention increases cardiac perfusion during arrhythmia episodes to ameliorate ischemia and avoid aggravation of arrhythmias into more dangerous forms.

Although the invention has been shown and described with reference to particular embodiments, it is to be understood that these embodiments are merely illustrative of the application of the principles of the invention. Numerous modifications may be made therein and other arrangements may be devised without departing from the true spirit and scope of the invention.

I claim:

1. An antiarrhythmia pacemaker for stimulating a patient's heart that has a skeletal muscle grafted to the cardiovascular system of the patient to assist cardiac functions of the heart, comprising:

means for detecting and classifying occurrences of at least one abnormal condition of the heart selected from the group comprising tachycardia, fibrillation and precursors of such tachycardia and fibrillation, heart stimulating means for generating and delivering stimulating pulses to the heart, at least one muscle stimulation electrode adapted to be placed in electrical contact with said muscle, muscle pulse stimulating means electrically coupled to said muscle stimulation electrode for generating and delivering stimulating pulse trains of sufficient energy to effect a desired contraction of said muscle, heart and muscle stimulation control means responsive to said detecting and classifying means for controlling said heart stimulating means and said muscle pulse stimulating means to direct a combined antiarrhythmia therapy and muscle stimulation therapy corresponding to the classification of the abnormal condition determined by said detecting and classifying means, wherein said detecting and classifying means detects ventricular tachycardia episodes and, in response to such detection and classification, said heart and muscle stimulation control means select and direct an appropriate antitachycardia pacing therapy in the form of timed electrical pulses generated and delivered by said heart stimulating means, and wherein in response to such tachycardia classification, said heart and muscle stimulation control means control said muscle pulse stimulating means to generate and deliver stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which a tachycardia condition is not detected in order to stimulate pulse trains of sufficient energy to effect a less frequent but stronger contraction of said muscle.

2. An antiarrhythmia pacemaker according to claim 1, wherein in response to such tachycardia classification, said heart and muscle stimulation control means control said muscle pulse stimulating means to generate and deliver stimulating pulse trains in which the time intervals between pulses of each pulse train gradually change from the beginning to the end of the pulse train.

3. An antiarrhythmia pacemaker according to claim 2, wherein in response to such tachycardia classification, said heart and muscle stimulation control means control said muscle pulse stimulating means to generate and deliver stimulating pulse trains in which the time intervals between pulses of each pulse train gradually decreases from the beginning to the end of the pulse train.

4. An antiarrhythmia pacemaker according to claim 2, wherein in response to such tachycardia classification, said heart and muscle stimulation control means control said muscle pulse stimulating means to generate and deliver stimulating pulse trains in which the time intervals between pulses of each pulse train gradually increases from the beginning to the end of the pulse train.

5. An antiarrhythmia pacemaker for stimulating a patient's heart that has a skeletal muscle grafted to the cardiovascular system of the patient to assist cardiac functions of the heart, comprising:

means for detecting and classifying occurrences of at least one abnormal condition of the heart selected from the group comprising tachycardia, fibrillation and precursors of such tachycardia and fibrillation, heart stimulating means for generating and delivering stimulating pulses to the heart, at least one muscle stimulation electrode adapted to be placed in electrical contact with said muscle, muscle pulse stimulating means electrically coupled to said muscle stimulation electrode for generating and delivering stimulating pulse trains of sufficient energy to effect a desired contraction of said muscle, heart and muscle stimulation control means responsive to said detecting and classifying means for controlling said heart stimulating means and said muscle pulse stimulating means to direct a combined antiarrhythmia therapy and muscle stimulation therapy corresponding to the classification of the abnormal condition determined by said detecting and classifying means, wherein said detecting and classifying means detects ventricular fibrillation episodes and, in response to such detection and classification, said heart and muscle stimulation control means select and direct an appropriate defibrillation therapy in the form of generation and delivery of at least one defibrillation shock, and wherein in response to such fibrillation classification, said heart and muscle stimulation control means, in cardiac cycles prior to the cardiac cycles within which defibrillation shocks are delivered, control said muscle pulse stimulating means to generate and deliver stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which a fibrillation condition is not detected in order to stimulate pulse trains of sufficient energy to effect a less frequent but stronger contraction of said muscle.

6. An antiarrhythmia pacemaker according to claim 5, wherein in response to such fibrillation classification, said heart and muscle stimulation control means control said muscle pulse stimulating means to generate and deliver stimulating pulse trains in which the time intervals between pulses of each pulse train gradually change from the beginning to the end of the pulse train.

7. An antiarrhythmia pacemaker according to claim 6, wherein in response to such fibrillation classification, said heart and muscle stimulation control means control said muscle pulse stimulating means to generate and deliver stimulating pulse trains in which the time intervals between pulses of each pulse train gradually decreases from the beginning to the end of the pulse train.

8. An antiarrhythmia pacemaker according to claim 6, wherein in response to such fibrillation classification, said heart and muscle stimulation control means control said muscle pulse stimulating means to generate and deliver stimulating pulse trains in which the time intervals between pulses of each pulse train gradually increases from the beginning to the end of the pulse train.

9. An antiarrhythmia pacemaker for stimulating a patient's heart that has a skeletal muscle grafted to the cardiovascular system of the patient to assist cardiac functions of the heart, comprising:

means for detecting and classifying occurrences of at least one abnormal condition of the heart selected from the group comprising tachycardia, fibrillation and precursors of such tachycardia and fibrillation, heart stimulating means for generating and delivering stimulating pulses to the heart, at least one muscle stimulation electrode adapted to be placed in electrical contact with said muscle, muscle pulse stimulating means electrically coupled to said muscle stimulation electrode for generating and delivering stimulating pulse trains of sufficient energy to effect a desired contraction of said muscle, heart and muscle stimulation control means responsive to said detecting and classifying means for controlling said heart stimulating means and said muscle pulse stimulating means to direct a combined antiarrhythmia therapy and muscle stimulation therapy corresponding to the classification of the abnormal condition determined by said detecting and classifying means, wherein said detecting and classifying means detects ventricular fibrillation episodes and, in response to such detection and classification, said heart and muscle stimulation control means select and direct an appropriate defibrillation therapy in the form of generation and delivery of at least one defibrillation shock, and wherein in response to such fibrillation classification, said heart and muscle stimulation control means, in cardiac cycles prior to and subsequent to the cardiac cycles within which defibrillation shocks are delivered, control said muscle pulse stimulating means to generate and deliver stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which a fibrillation condition is not detected in order to stimulate pulse trains of sufficient energy to effect a less frequent but stronger contraction of said muscle.

10. An antiarrhythmia pacemaker for stimulating a patient's hear that has a skeletal muscle grafted to the cardiovascular system of the patient to assist cardiac functions of the heart, comprising:

means for detecting and classifying occurrences of at least one abnormal condition of the heart selected from the group comprising tachycardia, fibrillation and precursors of such tachycardia and fibrillation, heart stimulating means for generating and delivering stimulating pulses to the heart, at least one muscle stimulation electrode adapted to be placed in electrical contact with said muscle, muscle pulse stimulating means electrically coupled to said muscle stimulation electrode for generating and delivering stimulating pulse trains of sufficient energy to effect a desired contraction of said muscle, heart and muscle stimulation control means responsive to said detecting and classifying means for controlling said heart stimulating means and said muscle pulse stimulating means to direct a combined antiarrhythmia therapy and muscle stimulation therapy corresponding to the classification of the abnormal condition determined by said detecting and classifying means, wherein each of said detecting and classifying means and said heart stimulating means function in both the atrial and ventricular chambers of the heart and wherein said detecting and classifying means detects atrial arrhythmia episodes and, in response to such detection and classification, said heart and muscle stimulation control means select and direct an appropriate antiarrhythmia pacing therapy in the form of timed electrical pulses generated and delivered by said heart stimulating means to at least one of said chambers of the heart, and wherein in response to such atrial arrhythmia classification, said heart and muscle stimulation control means control said muscle pulse stimulating means to generate and deliver stimulating pulse trains in which (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which an atrial arrhythmia condition is not detected in order to stimulate pulse trains of sufficient energy to effect a less frequent but stronger contraction of the muscle.

11. An antiarrhythmia pacemaker according to claim 10, wherein in response to such tachycardia classification, said heart and muscle stimulation control means control said muscle pulse stimulating means to generate and deliver stimulating pulse trains in which the time intervals between pulses of each pulse train gradually change from the beginning to the end of the pulse train.

12. An antiarrhythmia pacemaker for stimulating a patient's heart that has a skeletal muscle grafted to the cardiovascular system of the patient to assist cardiac functions of the heart, comprising:

means for detecting and classifying occurrences of at least one abnormal condition of the heart selected from the group comprising tachycardia, fibrillation and precursors of such tachycardia and fibrillation, heart stimulating means for generating and delivering stimulating pulses to the heart, at least one muscle stimulation electrode adapted to be placed in electrical contact with said muscle, muscle pulse stimulating means electrically coupled to said muscle stimulation electrode for generating and delivering stimulating pulse trains of sufficient energy to effect a desired contraction of said muscle, heart and muscle stimulation control means responsive to said detecting and classifying means for controlling said heart stimulating means and said muscle pulse stimulating means to direct a combined antiarrhythmia therapy and muscle stimulation therapy corresponding to the classification of the abnormal condition determined by said detecting and classifying means, wherein said detecting and classifying means detects precursors of malignant cardiac arrhythmias and wherein in response to such precursor classification, said heart and muscle stimulation control means control said muscle pulse stimulating means to generate and deliver stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which an arrhythmia precursor condition is not detected in order to stimulate pulse trains sufficient to effect a less frequent but stronger contraction of said muscle.

13. An antiarrhythmia pacemaker according to claim 12, wherein said precursors are selected from a group including ventricular tachycardia, ventricular couplets, premature ventricular complexes, premature ventricular depolarizations, repolarization abnormalities, ST-segment elevation, ST-segment depression and late potentials.

14. An antiarrhythmia pacemaker according to claim 12, wherein in response to such arrhythmia precursor classification, said heart and muscle stimulation control means control said muscle pulse stimulating means to generate and deliver stimulating pulse trains in which the time intervals between pulses of each pulse train gradually change from the beginning to the end of the pulse train.

15. A method for stimulating a patient's heart that has a skeletal muscle grafted to the cardiovascular system of the patient to assist cardiac functions of the heart, comprising the steps of:
   detecting and classifying occurrences of at least one abnormal condition of the heart selected from the group comprising tachycardia, fibrillation and precursors of such tachycardia and defibrillation,
   generating and delivering stimulating pulses to the heart,
   generating and delivering to said muscle stimulating pulse trains of sufficient energy to effect a desired contraction of said muscle,
   delivering said stimulation pulse trains to said muscle in synchrony with the contraction of the heart to augment and strengthen the heart in the absence of a detection of an abnormal condition of the heart during said detection and classification step, and delivering both antiarrhythmia therapy to the heart and stimulating pulse trains to said muscle upon detection of an abnormal condition of the heart during said detecting and classifying step, wherein during said detecting and classifying step ventricular tachycardia episodes are detected and, in response to such detection and classification, said delivering step selects and delivers an appropriate antitachycardia pacing therapy to the heart, and wherein in response to such tachycardia classification, said delivering step delivers pulse trains in which: (1) said pulse trains are synchronous to the timing of heart contractions but are generated for only a predetermined ratio of cardiac cycles to that the interval between muscle stimulation trains is greater than a predetermined tachycardia cycle interval, and (2) the duration of said pulse trains is greater than in the case in which a tachycardia condition is not detected in order to stimulate pulse trains of sufficient energy to effect a less frequent but stronger contraction of said muscle.

16. A method according to claim 15, wherein in response to such tachycardia classification, said delivering step generates and delivers stimulating pulse trains in which the time intervals between pulses of each pulse train gradually change from the beginning to the end of the pulse train.

17. A method for stimulating a patient's heart that has a skeletal muscle grafted to the cardiovascular system of the patient to assist cardiac functions of the heart, comprising the steps of:
   detecting and classifying occurrences of at least one abnormal condition of the heart selected from the group comprising tachycardia, fibrillation and precursors of such tachycardia and defibrillation,
   generating and delivering stimulating pulses to the heart,
   generating and delivering to said muscle stimulating pulse trains of sufficient energy to effect a desired contraction of said muscle,
   delivering said stimulation pulse trains to said muscle in synchrony with the contraction of the heart to augment and strengthen the heart in the absence of a detection of an abnormal condition of the heart during said detection and classification step, and delivering both antiarrhythmia therapy to the heart and stimulating pulse trains to said muscle upon detection of an abnormal condition of the heart during said detecting and classifying step, wherein during said detecting and classifying step ventricular fibrillation episodes are detected and, in response to such detection and classification, said delivering step selects and delivers an appropriate defibrillation therapy to the heart in the form of at least one defibrillation shock, and wherein in response to such fibrillation classification, said delivering step, in cardiac cycles prior to the cardiac cycles within which defibrillation shocks are delivered, delivers muscle stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which a fibrillation condition is not detected in order to stimulate pulse trains of sufficient energy to effect a less frequent but stronger contraction of the muscle.

18. A method for stimulating a patient's heart that has a skeletal muscle grafted to the cardiovascular system of the patient to assist cardiac functions of the heart, comprising the steps of:
   detecting and classifying occurrences of at least one abnormal condition of the heart selected from the group comprising tachycardia, fibrillation and precursors of such tachycardia and defibrillation,
   generating and delivering stimulating pulses to the heart,
   generating and delivering to said muscle stimulating pulse trains of sufficient energy to effect a desired contraction of said muscle,
   delivering said stimulation pulse trains to said muscle in synchrony with the contraction of the heart to augment and strengthen the heart in the absence of a detection of an abnormal condition of the heart during said detection and classification step, and delivering both antiarrhythmia therapy to the heart and stimulating pulse trains to said muscle upon detection of an abnormal condition of the heart during said detecting and classifying step, wherein during said detecting and classifying step arrhythmia precursor episodes are detected and, in response to such detection and classification, said delivering step selects and delivers an appropriate antiarrhythmia therapy to the heart in the form of stimulating pulses, and wherein in response to such arrhythmia precursor classification, said delivering step, in cardiac cycles prior to the cardiac cycles within which antiarrhythmia therapy is delivered, delivers skeletal muscle stimulating pulse trains in which: (1) said pulse trains are synchronous to the timing of heart contractions but are generated for only a predetermined ratio of cardiac cycles so that the interval between muscle stimulation trains is greater than a predetermined tachycardia cycle interval, and (2) the duration of said pulse trains is greater than in the case in which a fibrillation condition is not detected in order to stimulate pulse trains of sufficient energy to effect a less frequent but stronger contraction of the muscle.

19. A method according to claim 18, wherein said detected precursors are selected from a group including ventricular tachycardia, ventricular couplets, premature ventricular complexes, premature ventricular depolarizations, repolarization abnormalities, ST-segment elevation, ST-segment depression and late potentials.

* * * * *